US012594309B2

(12) United States Patent
Burcelin et al.

(10) Patent No.: US 12,594,309 B2
(45) Date of Patent: *Apr. 7, 2026

(54) BIFIDOBACTERIA FOR TREATING DIABETES AND RELATED CONDITIONS

(71) Applicant: INTERNATIONAL N&H DENMARK APS, Kongens Lyngby (DK)

(72) Inventors: Remy Burcelin, Escalquens (FR); Didier Carcano, Paris (FR); Sampo Lahtinen, Lohja (FI)

(73) Assignee: -International N&H Denmark Aps, Kongens Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/531,284

(22) Filed: Dec. 6, 2023

(65) Prior Publication Data

US 2025/0041358 A1     Feb. 6, 2025

Related U.S. Application Data

(63) Continuation of application No. 17/942,700, filed on Sep. 12, 2022, now abandoned, which is a continuation of application No. 17/180,028, filed on Feb. 19, 2021, now abandoned, which is a continuation of application No. 16/798,831, filed on Feb. 24, 2020, now abandoned, which is a continuation of application No. 16/211,743, filed on Dec. 6, 2018, now abandoned, which is a continuation of application No. 15/452,240, filed on Mar. 7, 2017, now abandoned, which is a continuation of application No. 13/377,325, filed as application No. PCT/IB2010/052757 on Jun. 18, 2010, now abandoned.

(60) Provisional application No. 61/218,563, filed on Jun. 19, 2009.

(51) Int. Cl.
| | |
|---|---|
| *A61K 35/745* | (2015.01) |
| *A23C 9/123* | (2006.01) |
| *A23L 33/135* | (2016.01) |
| *A61K 31/155* | (2006.01) |
| *A61K 31/715* | (2006.01) |
| *A61K 35/00* | (2006.01) |
| *A61K 35/747* | (2015.01) |
| *A61K 45/06* | (2006.01) |
| *A61P 3/04* | (2006.01) |
| *A61P 5/50* | (2006.01) |

(52) U.S. Cl.
CPC ........... *A61K 35/745* (2013.01); *A23C 9/123* (2013.01); *A23L 33/135* (2016.08); *A61K 31/155* (2013.01); *A61K 31/715* (2013.01); *A61K 35/747* (2013.01); *A61K 45/06* (2013.01); *A61P 3/04* (2018.01); *A61P 5/50* (2018.01); *A23V 2002/00* (2013.01); *A23V 2400/515* (2023.08); *A61K 2035/115* (2013.01); *A61K 2300/00* (2013.01); *Y02A 50/30* (2018.01)

(58) Field of Classification Search
None
See application file for complete search history.

(56) References Cited

FOREIGN PATENT DOCUMENTS

WO      WO-2009153662 A1 * 12/2009   ............. A61K 35/74

OTHER PUBLICATIONS

Gallwitz, Baptist. Review of Diabetic Studies. vol. 2, No. 2, p. 61-69, 2005.*
Charpentier et al. Diabetes Metab Res Rev 2002; 18:S70-S76.*

* cited by examiner

*Primary Examiner* — Oluwatosin A Ogunbiyi

(57) ABSTRACT

This invention relates to new uses of Bifidobacteria (particularly, although not exclusively, probiotic Bifidobacteria), and to food products, feed products, dietary supplements and pharmaceutical formulations containing them. The bacteria are suitable for the treatment of diabetes (particularly Type 2 diabetes), obesity and related conditions, metabolic syndrome, insulin resistance, and impaired glucose metabolism and consequences thereof, lowering tissue inflammation, treating hepatitis, myositis and cardiovascular conditions.

9 Claims, 12 Drawing Sheets

Intraperitoneal Glucose tolerance test

After four weeks of high fat diet

Intraperitoneal Glucose tolerance test

Four weeks after probiotic treatment

Insulin sensitivity: glucose infusion rates (mg/kg.min)

BIFIDOBACTERIA FOR TREATING DIABETES AND RELATED CONDITIONS

FIELD OF THE INVENTION

This invention relates to new uses of Bifidobacteria (particularly, although not exclusively, probiotic Bifidobacteria), and to food products, feed products, dietary supplements and pharmaceutical formulations containing them.

DESCRIPTION OF THE PRIOR ART

Diabetes mellitus, often referred to simply as diabetes, is a condition characterized by disordered metabolism and abnormally high blood sugar (hyperglycemia) resulting from insufficient levels and/or action of the hormone insulin. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy. These symptoms are likely to be less apparent if the blood sugar is only mildly elevated.

The World Health Organisation recognises three main forms of diabetes mellitus: type 1, type 2, and gestational diabetes (occurring during pregnancy), which have different causes and population distributions. While, ultimately, all forms are due to the beta cells of the pancreas being unable to produce sufficient insulin to prevent hyperglycemia, the causes are different. Type 1 diabetes is usually due to autoimmune destruction of the pancreatic beta cells. Type 2 diabetes is characterized by insulin resistance in target tissues. This causes a need for abnormally high amounts of insulin and diabetes develops when the beta cells cannot meet this demand. Gestational diabetes is similar to type 2 diabetes in that it involves insulin resistance; the hormones of pregnancy can cause insulin resistance in women genetically predisposed to developing this condition.

Gestational diabetes typically resolves with delivery of the child: however, types 1 and 2 diabetes are chronic conditions. All types have been treatable since insulin became medically available in 1921. Type 1 diabetes, in which insulin is not secreted by the pancreas, is directly treatable only with injected insulin, although dietary and other lifestyle adjustments are part of management. Type 2 may be managed with a combination of dietary treatment, tablets and injections and, frequently, insulin supplementation.

Diabetes can cause many complications. Acute complications (hypoglycemia, ketoacidosis or nonketotic hyperosmolar coma) may occur if the disease is not adequately controlled. Serious long-term complications include cardiovascular disease (doubled risk), chronic renal failure, retinal damage (which can lead to blindness), nerve damage (of several kinds), and microvascular damage, which may cause impotence and poor healing. Poor healing of wounds, particularly of the feet, can lead to gangrene, which may require amputation. Adequate treatment of diabetes, as well as increased emphasis on blood pressure control and lifestyle factors (such as not smoking and keeping a healthy body weight), may improve the risk profile of most aforementioned complications. In the developed world, diabetes is the most significant cause of adult blindness in the non-elderly and the leading cause of non-traumatic amputation in adults, and diabetic nephropathy is the main illness requiring renal dialysis in the United States.

Diabetes mellitus is currently a chronic disease, without a cure, and medical emphasis must necessarily be on managing/avoiding possible short-term as well as long-term diabetes-related problems. There is an exceptionally important role for patient education, dietetic support, sensible exercise, self glucose monitoring, with the goal of keeping both short-term blood glucose levels, and long term levels as well, within acceptable bounds. Careful control is needed to reduce the risk of long term complications. This is theoretically achievable with combinations of diet, exercise and weight loss (type 2), various oral diabetic drugs (type 2 only), and insulin use (type 1 and increasingly for type 2 not responding to oral medications). In addition, given the associated higher risks of cardiovascular disease, lifestyle modifications should be undertaken to control blood pressure and cholesterol by exercising more, smoking cessation, consuming an appropriate diet, wearing diabetic socks, and if necessary, taking any of several drugs to reduce pressure.

Oral antidiabetic drugs and insulin analogs currently on the market or undergoing clinical trials include biguanides (such as metformin), sulfonylureas (such as carbutamide, chlorpropamide, glibenclamide (Glyburide), gliclazide, glimepiride, glipizide, gliquidone, tolazamide or tolbutamide), alpha-glucosidase inhibitors (such as acarbose, miglitol or voglibose), thiazolidinediones (TZD) (such as pioglitazone, rivoglitazone or rosiglitazone), meglitinides (such as nateglinide, repaglinide or mitiglinide), dipeptidyl peptidase-4 (DPP-4) inhibitors (such as alogliptin, saxagliptin, sitagliptin or vildagliptin), glucagon-like peptide-1 analogs (such as exenatide, liraglutide, or albiglutide), amylin analogs (such as pramlintide), fast acting insulin analogs (such as insulin lispro, insulin aspart and insulin glulisine), long acting insulin analogs (such as insulin glargine, insulin detemir), dual PPAR agonists (such as aleglitazar) and SGLT2 inhibitors (such as dapagliflozin, remogliflozin and sergliflozin).

Type 2 diabetes is often associated with obesity. The body mass index (BMI) (calculated as weight in kilograms divided by the square of height in metres) is the most commonly accepted measurement for overweight and/or obesity. A BMI exceeding 25 is considered overweight. Obesity is defined as a BMI of 30 or more, with a BMI of 35 or more considered as serious comorbidity obesity and a BMI of 40 or more considered morbid obesity. Mortality is increased in obesity, with a BMI of over 32 being associated with a doubled risk of death. There are alterations in the body's response to insulin (insulin resistance), a proinflammatory state and an increased tendency to thrombosis (prothrombotic state).

Central obesity (male-type or waist-predominant obesity, characterised by a high waist-hip ratio), is a particularly important risk factor for diabetes and metabolic syndrome, the clustering of a number of diseases and risk factors that heavily predispose for cardiovascular disease. These are diabetes mellitus type 2, high blood pressure, high blood cholesterol, and triglyceride levels (combined hyperlipidemia).

The use of microorganisms in treating obesity, diabetes and diabetes-related conditions is in general known in the art. For example, WO 2007/043933 describes the use of probiotic bacteria for the manufacture of food and feed products, dietary supplements, for controlling weight gain, preventing obesity, increasing satiety, prolonging satiation, reducing food intake, reducing fat deposition, improving energy metabolism, enhancing insulin sensitivity, treating obesity and treating insulin insensitivity.

WO 2009/024429 describes the use of a primary composition comprising an agent that reduces the amount of proteobacteria, in particular enterobacteria and/or deferribacteres in the gut for the treatment or prevention of metabolic disorders, to support and/or to support weight management.

WO 2009/004076 describes the use of probiotic bacteria for normalising plasma glucose concentrations, improving insulin sensitivity, and reducing the risk of development in pregnant women, and preventing gestational diabetes.

WO 2009/021824 describes the use of probiotic bacteria, in particular *Lactobacillus rhamnosus*, to treat obesity, treat metabolic disorders, and support weight loss and/or weight maintenance.

WO 2008/016214 describes a probiotic lactic acid bacterium of the strain *Lactobacillus gasseri* BNR17 and its use in the inhibition of weight gain.

WO 02/38165 describes use of a strain of *Lactobacillus* (in particular, *Lactobacillus plantarum*) in reducing the risk factors involved in the metabolic syndrome.

US 2002/0037577 describes the use of microorganisms, such as Lactobacilli, for the treatment or prevention of obesity or diabetes mellitus by reduction of the amount of monosaccharide or disaccharide which may be absorbed into the body, by converting such compounds into polymeric materials which cannot be absorbed by the intestine.

Lee et al., *J. Appl. Microbiol.* 2007, 103, 1140-1146, describes the anti-obesity activity of trans-10, cis-12-conjugated linoleic acid (CLA)-producing bacterium of the strain *Lactobacillus plantarum* PL62 in mice.

Li et al., *Hepatology,* 2003, 37 (2), 343-350, describe the use of probiotics and anti-TNF antibodies in a mouse model for non-alcoholic fatty liver disease.

SUMMARY OF THE INVENTION

In one aspect, the invention comprises use of a bacterium of the genus *Bifidobacterium* or a mixture thereof in the manufacture of a food product, dietary supplement or medicament for treating diabetes (preferably but not exclusively Type 2 diabetes) in a mammal.

In another aspect, the invention comprises use of a bacterium of the genus *Bifidobacterium* or a mixture thereof in the manufacture of a food product, dietary supplement or medicament for treating impaired glucose tolerance in a mammal.

In a further aspect, the invention comprises use of a bacterium of the genus *Bifidobacterium* or a mixture thereof in the manufacture of a food product, dietary supplement or medicament for normalising insulin sensitivity in a mammal.

In a yet further aspect, the invention comprises use of a bacterium of the genus *Bifidobacterium* or a mixture thereof in the manufacture of a food product, dietary supplement or medicament for increasing fed insulin secretion in a mammal.

In a still further aspect, the invention comprises use of a bacterium of the genus *Bifidobacterium* or a mixture thereof in the manufacture of a food product, dietary supplement or medicament for decreasing fasted insulin secretion in a mammal.

In an additional aspect, the invention comprises use of a bacterium of the genus *Bifidobacterium* or a mixture thereof in the manufacture of a food product, dietary supplement or medicament for improving glucose tolerance in a mammal.

In another aspect, the invention comprises use of a bacterium of the genus *Bifidobacterium* or a mixture thereof in the manufacture of a food product, dietary supplement or medicament for treating obesity, controlling weight gain and/or inducing weight loss in a mammal.

In a further aspect, the invention comprises use of a bacterium of the genus *Bifidobacterium* or a mixture thereof in the manufacture of a food product, dietary supplement or medicament for lowering body fat mass in a mammal.

In a yet further aspect, the invention comprises use of a bacterium of the genus *Bifidobacterium* or a mixture thereof in the manufacture of a food product, dietary supplement or medicament for lowering mesenteric fat mass in a mammal.

In a still further aspect, the invention comprises use of a bacterium of the genus *Bifidobacterium* or a mixture thereof in the manufacture of a food product, dietary supplement or medicament for lowering tissue inflammation (particularly, although not exclusively, muscle tissue inflammation, liver tissue inflammation and/or adipose tissue inflammation) in a mammal.

In a still further aspect, the invention comprises use of a bacterium of the genus *Bifidobacterium* or a mixture thereof in the manufacture of a food product, dietary supplement or medicament for treating hepatitis in a mammal.

In a yet further aspect, the invention comprises use of a bacterium of the genus *Bifidobacterium* or a mixture thereof in the manufacture of a food product, dietary supplement or medicament for treating myositis in a mammal.

In a still further aspect, the invention comprises use of a bacterium of the genus *Bifidobacterium* or a mixture thereof in the manufacture of a food product, dietary supplement or medicament for treating cardiovascular disease in a mammal.

In a yet further aspect, the invention comprises use of a bacterium of the genus *Bifidobacterium* or a mixture thereof in the manufacture of a food product, dietary supplement or medicament for treating metabolic syndrome in a mammal.

In another aspect, the invention comprises a bacterium of the genus *Bifidobacterium* or a mixture thereof for use in treating diabetes (particularly, although not exclusively, Type 2 diabetes) in a mammal.

In a further aspect, the invention comprises a bacterium of the genus *Bifidobacterium* or a mixture thereof for use in treating impaired glucose tolerance in a mammal.

In a yet further aspect, the invention comprises a bacterium of the genus *Bifidobacterium* or a mixture thereof for use in normalising insulin sensitivity in a mammal.

In a still further aspect, the invention comprises a bacterium of the genus *Bifidobacterium* or a mixture thereof for use in increasing fed insulin secretion in a mammal.

In another aspect, the invention comprises a bacterium of the genus *Bifidobacterium* or a mixture thereof for use in decreasing fasted insulin secretion in a mammal.

In a further aspect, the invention comprises a bacterium of the genus *Bifidobacterium* or a mixture thereof for use in improving glucose tolerance in a mammal.

In a yet further aspect, the invention comprises a bacterium of the genus *Bifidobacterium* or a mixture thereof for use in treating obesity, controlling weight gain and/or inducing weight loss in a mammal.

In another aspect, the invention comprises a bacterium of the genus *Bifidobacterium* or a mixture thereof for use in lowering body fat mass in a mammal.

In a further aspect, the invention comprises a bacterium of the genus *Bifidobacterium* or a mixture thereof for use in lowering mesenteric fat mass in a mammal.

In a yet further aspect, the invention comprises a bacterium of the genus *Bifidobacterium* or a mixture thereof for use in lowering tissue inflammation (particularly, although not exclusively, muscle tissue inflammation, liver tissue inflammation and/or adipose tissue inflammation) in a mammal.

In a still further aspect, the invention comprises a bacterium of the genus *Bifidobacterium* or a mixture thereof for use in treating hepatitis in a mammal.

In a yet further aspect, the invention comprises a bacterium of the genus *Bifidobacterium* or a mixture thereof for use in treating myositis in a mammal.

In a still further aspect, the invention comprises a bacterium of the genus *Bifidobacterium* or a mixture thereof for use in treating cardiovascular disease in a mammal.

In a still further aspect, the invention comprises a bacterium of the genus *Bifidobacterium* or a mixture thereof for use in treating metabolic syndrome in a mammal.

In another aspect, the invention comprises a method of treating diabetes (particularly although not exclusively Type 2 diabetes) in a mammal, comprising administering to a mammal in need of such treatment a bacterium of the genus *Bifidobacterium* or a mixture thereof.

In a further aspect, the invention comprises a method of treating impaired glucose tolerance in a mammal, comprising administering to a mammal in need thereof a bacterium of the genus *Bifidobacterium* or a mixture thereof.

In a yet further aspect, the invention comprises a method of normalising insulin sensitivity in a mammal, comprising administering to a mammal in need thereof a bacterium of the genus *Bifidobacterium* or a mixture thereof.

In a still further aspect, the invention comprises a method of increasing fed insulin secretion in a mammal, comprising administering to a mammal in need thereof a bacterium of the genus *Bifidobacterium* or a mixture thereof.

In another aspect, the invention comprises a method of decreasing fasted insulin secretion in a mammal, comprising administering to a mammal in need thereof a bacterium of the genus *Bifidobacterium* or a mixture thereof.

In a further aspect, the invention comprises a method of improving glucose tolerance in a mammal, comprising administering to a mammal in need thereof a bacterium of the genus *Bifidobacterium* or a mixture thereof.

In a yet further aspect, the invention comprises a method of treating obesity, controlling weight gain and/or inducing weight loss in a mammal, comprising administering to a mammal in need of such treatment a bacterium of the genus *Bifidobacterium* or a mixture thereof.

In a still further aspect, the invention comprises a method of lowering body fat mass in a mammal, comprising administering to a mammal in need thereof a bacterium of the genus *Bifidobacterium* or a mixture thereof.

In another aspect, the invention comprises a method of lowering mesenteric fat mass in a mammal, comprising administering to a mammal in need thereof a bacterium of the genus *Bifidobacterium* or a mixture thereof.

In a further aspect, the invention comprises a method of lowering tissue inflammation (particularly, although not exclusively, muscle tissue inflammation, liver tissue inflammation and/or adipose tissue inflammation) in a mammal, comprising administering to a mammal in need thereof a bacterium of the genus *Bifidobacterium* or a mixture thereof.

In a yet further aspect, the invention comprises a method of treating hepatitis in a mammal, comprising administering to a mammal in need thereof a bacterium of the genus *Bifidobacterium* or a mixture thereof.

In a still further aspect, the invention comprises a method of treating myositis in a mammal, comprising administering to a mammal in need thereof a bacterium of the genus *Bifidobacterium* or a mixture thereof.

In a yet further aspect, the invention comprises a method of treating cardiovascular disease in a mammal, comprising administering to a mammal in need thereof a bacterium of the genus *Bifidobacterium* or a mixture thereof.

In a still further aspect, the invention comprises a method of treating metabolic syndrome in a mammal, comprising administering to a mammal in need of such treatment a bacterium of the genus *Bifidobacterium* or a mixture thereof.

DETAILED DESCRIPTION OF THE INVENTION

Bacteria

Figure 1:
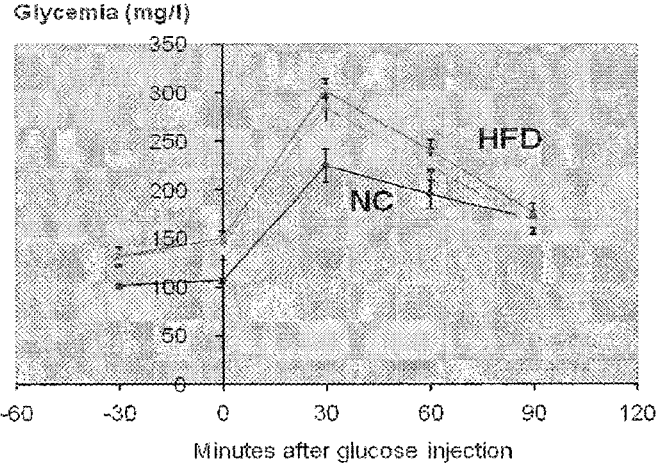
FIG. 1 illustrates the results of an intraperitoneal glucose tolerance test in adult male C57bl6 mice fed a high fat diet (HFD) for four weeks or a normal chow (NC)

The bacterium used in the present invention is selected from a *Bifidobacterium* or a mixture thereof. Preferably the *Bifidobacterium* to be used in the present invention is a *Bifidobacterium* which is generally recognised as safe and, which is preferably GRAS approved.

The bacterium may be used in any form capable of exerting the effects described herein. For example, the bacteria may be viable, dormant, inactivated or dead bacteria. Preferably, the bacteria are viable bacteria.

The bacteria may comprise whole bacteria or may comprise bacterial components. Examples of such components include bacterial cell wall components such as peptidoglycan, bacterial nucleic acids such as DNA and RNA, bacterial membrane components, and bacterial structural components such as proteins, carbohydrates, lipids and combinations of these such as lipoproteins, glycolipids and glycoproteins.

The bacteria may also or alternatively comprise bacterial metabolites. In this specification the term 'bacterial metabolites' includes all molecules produced or modified by the (probiotic) bacteria as a result of bacterial metabolism during growth, survival, persistence, transit or existence of bacteria during probiotic product manufacture and storage and during gastrointestinal transit in a mammal. Examples include all organic acids, inorganic acids, bases, proteins and peptides, enzymes and co-enzymes, amino acids and nucleic acids, carbohydrates, lipids, glycoproteins, lipoproteins, glycolipids, vitamins, all bioactive compounds, metabolites containing an inorganic component, and all small molecules, for example nitrous molecules or molecules containing a *sulphurous* acid.

Preferably the bacteria comprise whole bacteria, more preferably whole viable bacteria.

Preferably, the *Bifidobacterium* used in accordance with the present invention is one which is suitable for human and/or animal consumption. A skilled person will be readily aware of specific species and or strains of Bifidobacteria from within the genera described herein which are used in the food and/or agricultural industries and which are generally considered suitable for human and/or animal consumption.

In the present invention, the *Bifidobacterium* used may be of the same type (species and strain) or may comprise a mixture of species and/or strains.

Suitable Bifidobacteria are selected from the species *Bifidobacterium lactis*, *Bifidobacterium bifidium*, *Bifidobacterium longum*, *Bifidobacterium animalis*, *Bifidobacterium breve*, *Bifidobacterium infantis*, *Bifidobacterium catenulatum*, *Bifidobacterium pseudocatenulatum*, *Bifidobacterium adolescentis*, and *Bifidobacterium angulatum*, and combinations of any thereof.

Preferably, the *Bifidobacterium* used in the present invention is of the species *Bifidobacterium animalis*. More preferably, the *Bifidobacterium* used in the present invention is of the species *Bifidobacterium animalis* subsp. *lactis*.

In a particularly preferred embodiment, the bacteria used in the present invention are *Bifidobacterium animalis* subsp. *lactis* strain 420 (B420). This strain is commercially available from Danisco A/S.

In one embodiment, the bacterium used in the present invention is a probiotic bacterium. In this specification the term 'probiotic bacterium' is defined as covering any non-pathogenic bacterium which, when administered live in adequate amounts, confer a health benefit on the host. These probiotic strains generally have the ability to survive the passage through the upper part of the digestive tract. They are non-pathogenic, non-toxic and exercise their beneficial effect on health on the one hand via ecological interactions with the resident flora in the digestive tract, and on the other hand via their ability to influence the immune system in a positive manner via the "GALT" (gut-associated lymphoid tissue). Depending on the definition of probiotics, these bacteria, when given in a sufficient number, have the ability to progress live through the intestine, however they do not cross the intestinal barrier and their primary effects are therefore induced in the lumen and/or the wall of the gastrointestinal tract. They then form part of the resident flora during the administration period. This colonization (or transient colonization) allows the probiotic bacteria to exercise a beneficial effect, such as the repression of potentially pathogenic micro-organisms present in the flora and interactions with the immune system of the intestine.

In preferred embodiments, the bacterium used in the present invention is a probiotic *Bifidobacterium*.

In some embodiments, the *Bifidobacterium* is used in the present invention together with a bacterium of the genus *Lactobacillus*. A combination of *Bifidobacterium* and *Lactobacillus* bacteria according to the present invention exhibits a synergistic effect in certain applications (i.e. an effect which is greater than the additive effect of the bacteria when used separately). For example, combinations which, in addition to having effect on the mammal as single components, may have beneficial effect on the other components of the combination, for example by producing metabolites which are then in turn used as an energy source by other components of the combination, or maintaining physiological conditions which favour the other components.

Typically, the *Lactobacillus* bacteria are selected from the species *Lactobacillus acidophilus*, *Lactobacillus casei*, *Lactobacillus kefiri*, *Lactobacillus bifidus*, *Lactobacillus brevis*, *Lactobacillus helveticus*, *Lactobacillus paracasei*, *Lactobacillus rhamnosus*, *Lactobacillus salivarius*, *Lactobacillus curvatus*, *Lactobacillus bulgaricus*, *Lactobacillus sakei*, *Lactobacillus reuteri*, *Lactobacillus fermentum*, *Lactobacillus farciminis*, *Lactobacillus lactis*, *Lactobacillus delbreuckii*, *Lactobacillus plantarum*, *Lactobacillus paraplantarum*, *Lactobacillus crispatus*, *Lactobacillus gasseri*, *Lactobacillus johnsonii* and *Lactobacillus jensenii*, and combinations of any thereof.

In preferred embodiments, the *Lactobacillus* bacterium used in the present invention is a probiotic *Lactobacillus*.

Preferably, the *Lactobacillus* bacterium used in the present invention of the species *Lactobacillus acidophilus*.

In a preferred embodiment, the *Bifidobacterium* is used in the present invention together with a bacterium of the species *Lactobacillus acidophilus* strain NCFM. *Lactobacillus acidophilus* NCFM was deposited by Rhodia Chimie, France, at the American Type Culture Collection as PTA-4797 on 15 Nov. 2002.

In a particularly preferred embodiment, the bacteria used in the present invention comprise a combination of *Bifidobacterium animalis* subsp. *lactis* strain 420 (B420) and *Lactobacillus acidophilus* strain NCFM (PTA-4797).

Dosage

The *Bifidobacterium* (such as a strain of *Bifidobacterium animalis* subsp. *lactis*, for example *Bifidobacterium animalis* subsp. *lactis* strain 420 (B420), and (if present) the *Lactobacillus* (such as a strain of *Lactobacillus acidophilus*, for example *Lactobacillus acidophilus* strain NCFM) used in accordance with the present invention may comprise from $10^6$ to $10^{12}$ CFU of bacteria/g of support, and more particularly from $10^8$ to $10^{12}$ CFU of bacteria/g of support, preferably $10^9$ to $10^{12}$ CFU/g for the lyophilized form.

Suitably, the *Bifidobacterium* (such as a strain of *Bifidobacterium animalis* subsp. *lactis*, for example *Bifidobacterium animalis* subsp. *lactis* strain 420 (B420), and (if present) the *Lactobacillus* (such as a strain of *Lactobacillus acidophilus*, for example *Lactobacillus acidophilus* strain NCFM), may be administered at a dosage of from about $10^6$ to about $10^{12}$ CFU of microorganism/dose, preferably about $10^8$ to about $10^{12}$ CFU of microorganism/dose. By the term "per dose" it is meant that this amount of microorganism is provided to a subject either per day or per intake, preferably per day. For example, if the microorganism is to be administered in a food product (for example in a yoghurt)—then the yoghurt will preferably contain from about $10^8$ to $10^{12}$ CFU of the microorganism. Alternatively, however, this amount of microorganism may be split into multiple administrations each consisting of a smaller amount of microbial loading-so long as the overall amount of microorganism received by the subject in any specific time (for instance each 24 hour period) is from about $10^6$ to about $10^{12}$ CFU of microorganism, preferably $10^8$ to about $10^{12}$ CFU of microorganism.

In accordance with the present invention an effective amount of at least one strain of a microorganism may be at least $10^6$ CFU of microorganism/dose, preferably from about $10^6$ to about $10^{12}$ CFU of microorganism/dose, preferably about $10^8$ to about $10^{12}$ CFU of microorganism/dose.

In one embodiment, preferably the *Bifidobacterium* (such as a strain of *Bifidobacterium animalis* subsp. *lactis*, for example *Bifidobacterium animalis* subsp. *lactis* strain 420 (B420), and (if present) the *Lactobacillus* (such as a strain of *Lactobacillus acidophilus*, for example *Lactobacillus acidophilus* strain NCFM), may be administered at a dosage of from about $10^6$ to about $10^{12}$ CFU of microorganism/day, preferably about $10^8$ to about $10^{12}$ CFU of microorganism/day. Hence, the effective amount in this embodiment may be from about $10^6$ to about $10^{12}$ CFU of microorganism/day, preferably about $10^8$ to about $10^{12}$ CFU of microorganism/day.

CFU stands for "colony-forming units". By 'support' is meant the food product, dietary supplement or the pharmaceutically acceptable support.

When Bifidobacteria are used in the present invention together with Lactobacilli, the bacteria may be present in any ratio capable of achieving the desired effects of the invention described herein. Typically, the Bifidobacteria to Lactobacilli ratio (measured in terms of colony forming units) is in the range 1:100 to 100:1, suitably 1:50 to 50:1, preferably 1:20 to 20:1, more preferably 1:10 to 10:1, still more preferably 1:5 to 5:1, yet more preferably 1:3 to 3:1 and even more preferably 1:2 to 2:1 and most preferably 1:1.5 to 1.5:1. In a particular example, the Bifidobacteria to Lactobacilli ratio is 1:1.

In particular, when Bifidobacteria *animalis* subsp. *lactis* strain 420 (B420) bacteria are used in the present invention together with *Lactobacillus acidophilus* strain NCFM bacteria, the bacteria may be present in any ratio capable of achieving the desired effects of the invention described herein. Typically, the ratio of Bifidobacteria *animalis* subsp. *lactis* strain 420 to *Lactobacillus acidophilus* strain NCFM (measured in terms of colony forming units) is in the range is in the range 1:100 to 100:1, suitably 1:50 to 50:1, preferably 1:20 to 20:1, more preferably 1:10 to 10:1, still more preferably 1:5 to 5:1, yet more preferably 1:3 to 3:1 and even more preferably 1:2 to 2:1 and most preferably 1:1.5 to 1.5:1. In a particular example, the Bifidobacteria *animalis* subsp. *lactis* strain 420 to *Lactobacillus acidophilus* strain NCFM ratio is 1:1.

Subjects/Medical Indications

The Bifidobacteria (and, if present, the Lactobacilli) to which the present invention relates are administered to a mammal, including for example livestock (including cattle, horses, pigs, chickens and sheep), and humans. In some aspects of the present invention the mammal is a companion animal (including pets), such as a dog or a cat for instance. In some aspects of the present invention, the subject may suitably be a human.

The Bifidobacteria (and, if present, the Lactobacilli) to which the present invention relates may be suitable for treating a number of diseases or conditions in mammals (particularly humans). In this specification the term "treatment" or "treating" refers to any administration of the Bifidobacteria (and, if present, Lactobacilli) according to the present invention and includes: (1) preventing the specified disease from occurring in a mammal which may be predisposed to the disease but does not yet experience or display the pathology or symptomatology of the disease (including prevention of one or more risk factors associated with the disease); (2) inhibiting the disease in a mammal that is experiencing or displaying the pathology or symptomatology of the diseased (i.e., arresting further development of the pathology and/or symptomatology), or (3) ameliorating the disease in a mammal that is experiencing or displaying the pathology or symptomatology of the diseased (i.e., reversing the pathology and/or symptomatology).

The Bifidobacteria to which the present invention relates are suitable for administration to both diabetic and obese mammals. They could also be suitable for diabetic and non-obese mammals, as well as to obese mammals possessing the risk factors for diabetes, but not yet in a diabetic state. This aspect is discussed in more detail below.

In particular, the use of Bifidobacteria according to the present invention is suitable for the treatment of mammals ingesting a high-fat diet. This aspect is discussed in more detail below.

As described in more detail in the Examples below, the Bifidobacteria used in the present invention have a number of biological activities. In particular, the Bifidobacteria used in the present invention are capable of normalising insulin sensitivity, increasing fed insulin secretion, decreasing fasted insulin secretion, improving glucose tolerance in a mammal. These effects confer the potential for use in the treatment of diabetes and diabetes-related conditions (in particular, Type 2 diabetes and impaired glucose tolerance).

In particular, as described in more detail in the Examples below, the Bifidobacteria used in combination with *Lactobacillus* bacteria (particularly *Lactobacillus acidophilus* bacteria) in accordance with the present invention have a number of biological activities. In particular, the Bifidobacteria used in the present invention are capable of increasing fed insulin secretion and improving glucose tolerance in a mammal. These effects confer the potential for use in the treatment of diabetes and diabetes-related conditions (in particular, Type 2 diabetes and impaired glucose tolerance).

In this specification the term 'diabetes' includes all forms of diabetes which, as noted above, is characterised by disordered metabolism and abnormally high blood sugar (hyperglycemia) resulting from insufficient levels of the hormone insulin. The term therefore includes Type 1 diabetes, Type 2 diabetes, gestational diabetes, and impaired glucose tolerance. Type 1 diabetes is characterised by loss of the insulin-producing beta cells of the islets of Langerhans in the pancreas, leading to a deficiency of insulin. Type 2 diabetes mellitus is characterised by insulin resistance or reduced insulin sensitivity, combined with reduced insulin secretion. Gestational diabetes is formally defined as "any degree of glucose intolerance with onset or first recognition during pregnancy". Impaired Glucose Tolerance (IGT) is a pre-diabetic state of dysglycemia that is associated with insulin resistance and increased risk of cardiovascular pathology. According to the criteria of the World Health Organization and the American Diabetes Association, impaired glucose tolerance is defined as two-hour glucose levels of 140 to 199 mg per dL (7.8 to 11.0 mmol) on the 75-g oral glucose tolerance test. A patient is said to be under the condition of IGT when he/she has an intermediately raised glucose level after 2 hours, but less than would qualify for type 2 diabetes mellitus. The fasting glucose may be either normal or mildly elevated. IGT may precede type 2 diabetes mellitus by many years. IGT is also a risk factor for mortality.

In addition, the Bifidobacteria used in the present invention are capable of inducing weight loss and lowering body fat mass (in particular, mesenteric fat mass). These effects confer the potential for use in the treatment of obesity and controlling weight gain and/or inducing weight loss in a mammal.

In particular, as described in more detail in the Examples below, the Bifidobacteria used in combination with *Lactobacillus* bacteria (particularly *Lactobacillus acidophilus* bacteria) in accordance with the present invention are capable of inducing weight loss and lowering body fat mass (in particular, mesenteric fat mass). These effects confer the potential for use in the treatment of obesity and controlling weight gain and/or inducing weight loss in a mammal.

In this specification, the term obesity is linked to body mass index (BMI). The body mass index (BMI) (calculated as weight in kilograms divided by the square of height in metres) is the most commonly accepted measurement for overweight and/or obesity. A BMI exceeding 25 is considered overweight. Obesity is defined as a BMI of 30 or more, with a BMI of 35 or more considered as serious comorbidity obesity and a BMI of 40 or more considered morbid obesity.

As noted above, the term "obesity" as used herein includes obesity, comorbidity obesity and morbid obesity. Therefore, the term "obese" as used here may be defined as a subject having a BMI of more than or equal to 30. In some embodiments, suitably an obese subject may have a BMI of more than or equal to 30, suitably 35, suitably 40.

While the composition of the invention is particularly suitable for use in patients who are both diabetic and obese, the composition is also suitable for those who are diabetic but not obese. It may also be suitable for use in obese patients possessing the risk factors for diabetes, but not yet in a diabetic state, as it could be expected that an obese person (but not diabetic), could limit the metabolic consequences of his obesity, i.e. the diabetes or at least insulino-resistance development.

In addition, the Bifidobacteria used in the present invention may be used for treating metabolic syndrome in a mammal. Metabolic syndrome is a combination of medical disorders that increase the risk of developing cardiovascular disease and diabetes. Metabolic syndrome is also known as metabolic syndrome X, syndrome X, insulin resistance syndrome, Reaven's syndrome or CHAOS (Australia).

There is currently no single accepted definition of metabolic syndrome. The World Health Organization criteria (1999) require presence of diabetes mellitus, impaired glucose tolerance, impaired fasting glucose or insulin resistance, AND two of the following:

blood pressure: ≥140/90 mmHg dyslipidemia: triglycerides (TG): ≥1.695 mmol/L and high-density lipoprotein cholesterol (HDL-C)≤0.9 mmol/L (male), ≤1.0 mmol/L (female)

central obesity: waist:hip ratio >0.90 (male); >0.85 (female), and/or body mass index>30 kg/m$^2$ microalbuminuria: urinary albumin excretion ratio ≥20 mg/min or albumin:creatinine ratio ≥30 mg/g.

The European Group for the Study of Insulin Resistance (1999) requires insulin resistance defined as the top 25% of the fasting insulin values among non-diabetic individuals AND two or more of the following:

central obesity: waist circumference ≥94 cm (male), ≥80 cm (female)

dyslipidemia: TG≥2.0 mmol/L and/or HDL-C<1.0 mg/dL or treated for dyslipidemia hypertension: blood pressure ≥140/90 mmHg or antihypertensive medication fasting plasma glucose ≥6.1 mmol/L The US National Cholesterol Education Program (NCEP) Adult Treatment Panel III (2001) requires at least three of the following:

central obesity: waist circumference ≥102 cm or 40 inches (male), ≥88 cm or 36 inches (female)

dyslipidemia: TG≥1.695 mmol/L (150 mg/dl)

dyslipidaemia: HDL-C<40 mg/dl (male), <50 mg/dL (female)

blood pressure ≥130/85 mmHg fasting plasma glucose ≥6.1 mmol/L (110 mg/dl)

In further embodiments, the Bifidobacteria (and, if present, the Lactobacilli) used in the present invention may be used to lower tissue inflammation (particularly, although not exclusively, liver tissue inflammation, muscle tissue inflammation and/or adipose tissue inflammation) in a mammal.

In one embodiment, the Bifidobacteria (and, if present, the Lactobacilli) used in the present invention may be used to lower liver tissue inflammation. This confers the potential for the application of the bacteria in the treatment of hepatitis, which is characterised by the destruction of a number of liver cells and the presence of inflammatory cells in the liver tissue.

Hepatitis can be divided into two subgroups according to its duration: acute hepatitis (lasting less than six months) and chronic hepatitis (lasting longer than six months). Hepatitis may be also classified according to its cause: for example, hepatitis may comprise Infectious viral hepatitis (such as hepatitis A, hepatitis B, hepatitis C, hepatitis D and hepatitis E), hepatitis caused by other viral diseases (such as mononucleosis and cytomegalovirus), hepatitis caused by severe bacterial infections or amoebic infections. hepatitis caused by medicines, hepatitis caused by toxins such as alcohol, autoimmune hepatitis (in which a number of liver cells are destroyed by the patient's own immune system) and hepatitis caused by congenital metabolic disorders, such as Wilson's disease (disorder of the body's copper metabolism) and haemochromatosis (disorder of the body's iron metabolism).

In one embodiment, the Bifidobacteria (and, if present, the Lactobacilli) used in the present invention may be used to lower muscle tissue inflammation. This confers the potential for the application of the bacteria in the treatment of myositis, in which the muscle fibers and skin are inflamed and damaged, resulting in muscle weakness.

There are several types of myositis that affect different parts of the body. Particular forms of myositis treatable according to the present invention include: polymyositis (PM) (in which muscles in many parts of the body, and especially those parts closest to the trunk, are inflamed); dermatomyositis (DM) (which affects both the muscle fibers and skin by damaging capillaries that supply blood to the muscle and skin), inclusion body myositis (IBM) which is characterized by gradual weakening of muscles throughout the body, including the wrists or fingers, development of dysphagia, and atrophy of forearms and/or thigh muscles; and juvenile myositis (JM), which involves muscle weakness, skin rash, and dysphagia in children.

The present inventors have surprisingly found that the Bifidobacteria (and, if present, the Lactobacilli) to which the present invention relates are capable of lowering adipose tissue inflammation in mammals. There is epidemiological evidence in the literature showing a statistical relationship between inflammation, obesity and insulin resistance in humans (Cani et al., *Diabetes*, 2007, 56, 1761-1772, and references cited therein). This finding therefore confers the potential for the Bifidobacteria (and, if present, the Lactobacilli) to be useful in the treatment of obesity, diabetes and related conditions, metabolic diseases and cardiovascular consequences in mammals.

According to Berg and Scherer, *Circulation Research*, 2005, 96, 939, recent evidence highlights the role of adipose tissue in the development of a systemic inflammatory state that contributes to obesity-associated vasculopathy and cardiovascular risk. Circulating mediators of inflammation participate in the mechanisms of vascular insult and atheromatous change, and many of these inflammatory proteins are secreted directly from adipocytes and adipose tissue-derived macrophages. Several factors linking obesity with an increased cardiovascular risk have been identified. The adipocyte-specific secretory protein adiponectin is a particularly promising candidate in this context. Its levels are decreased in obesity.

The targeted suppression of various proinflammatory cascades in adipocytes specifically represents a new therapeutic opportunity for the cardiovascular disease area. Suppression of adipose tissue inflammation would therefore be expected to provide a therapeutic benefit in the treatment of cardiovascular diseases.

Examples of cardiovascular diseases treatable by use of the Bifidobacteria (and, if present, the Lactobacilli) according to the present invention include aneurysm, angina, atherosclerosis, cerebrovascular accident (stroke), cerebrovascular disease, congestive heart failure (CHF), coronary artery disease, myocardial infarction (heart attack) and peripheral vascular disease.

An aneurysm is a localized, blood-filled dilation (balloon-like bulge) of a blood vessel caused by disease or weakening of the vessel wall. Aneurysms most commonly occur in arteries at the base of the brain (the circle of Willis) and in the aorta (the main artery coming out of the heart, a so-called aortic aneurysm). As the size of an aneurysm increases, there is an increased risk of rupture, which can result in severe hemorrhage or other complications including sudden death.

Angina pectoris, commonly known as angina, is severe chest pain due to ischemia (a lack of blood and hence oxygen supply) of the heart muscle, generally due to obstruction or spasm of the coronary arteries (the heart's blood vessels). Coronary artery disease, the main cause of angina, is due to atherosclerosis of the cardiac arteries.

Atherosclerosis is the condition in which an artery wall thickens as the result of a build up of fatty materials such as cholesterol. It is a syndrome affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a hardening or furring of the arteries. It is caused by the formation of multiple plaques within the arteries.

A stroke is the rapidly developing loss of brain function(s) due to disturbance in the blood supply to the brain. This can be due to ischemia (lack of blood supply) caused by thrombosis or embolism or due to a hemorrhage. As a result, the affected area of the brain is unable to function, leading to inability to move one or more limbs on one side of the body, inability to understand or formulate speech, or see one side of the visual field and ultimately to death.

Cerebrovascular disease is a group of brain dysfunctions related to disease of blood vessels supplying the brain. Hypertension is the most important cause that damages the blood vessel lining endothelium exposing the underlying collagen where platelets aggregate to initiate a repairing process which is not always complete and perfect. Sustained hypertension permanently changes the architecture of the blood vessels making them narrow, stiff, deformed and uneven which are more vulnerable to fluctuations of blood pressure. A fall in blood pressure during sleep can lead to marked reduction in blood flow in the narrowed blood vessels causing ischemic stroke in the morning whereas a sudden rise in blood pressure can cause tearing of the blood vessels causing intracranial hemorrhage during excitation at daytime. Primarily people who are elderly, diabetic, smoker, or have ischemic heart disease, have cerebrovascular disease. All diseases related to artery dysfunction can be classified under a disease as known as macrovascular disease. This is a simplistic study by which arteries are blocked by fatty deposits or by a blood clot. The results of cerebrovascular disease can include a stroke, or even sometimes a hemorrhagic stroke. Ischemia or other blood vessel dysfunctions can affect one during a cerebrovascular accident.

Heart failure is a global term for the physiological state in which cardiac output is insufficient for the body's needs. This may occur when the cardiac output is low (often termed "congestive heart failure"). Common causes of heart failure include myocardial infarction and other forms of ischemic heart disease, hypertension, valvular heart disease and cardiomyopathy.

Coronary disease (or coronary heart disease) refers to the failure of coronary circulation to supply adequate circulation to cardiac muscle and surrounding tissue. It is most commonly equated with atherosclerotic coronary artery disease, but coronary disease can be due to other causes, such as coronary vasospasm. It is possible for the stenosis to be caused by the spasm.

Myocardial infarction, commonly known as a heart attack, occurs when the blood supply to part of the heart is interrupted causing some heart cells to die. This is most commonly due to occlusion (blockage) of a coronary artery following the rupture of a vulnerable atherosclerotic plaque, which is an unstable collection of lipids (like cholesterol) and white blood cells (especially macrophages) in the wall of an artery. The resulting ischemia (restriction in blood supply) and oxygen shortage, if left untreated for a sufficient period of time, can cause damage and/or death (infarction) of heart muscle tissue (myocardium).

Peripheral vascular disease (PVD), also known as peripheral artery disease (PAD) or peripheral artery occlusive disease (PAOD), includes all diseases caused by the obstruction of large arteries in the arms and legs. PVD can result from atherosclerosis, inflammatory processes leading to stenosis, an embolism or thrombus formation. It causes either acute or chronic ischemia (lack of blood supply), typically of the legs.

It is envisaged within the scope of the present invention that the embodiments of the invention can be combined such that combinations of any of the features described herein are included within the scope of the present invention. In particular, it is envisaged within the scope of the present invention that any of the therapeutic effects of the bacteria may be exhibited concomitantly.

Diet

As noted above, diabetic and/or obese mammals treated with bacteria according to the present invention may ingest a high-fat diet while mitigating the metabolic consequences of their condition(s). In this specification the term 'high-fat diet' means a diet generally containing at least 20%, preferably at least 25%, such as at least 30%, for example at least 35%, such as at least 40%, for example at least 45%, such as at least 50%, for example at least 55%, such as at least 60%, for example at least 65%, such as at least 70%, for example at least 75%, such as at least 80%, for example at least 85%, such as at least 90% of calories from fat.

In some embodiments, mammals treated with bacteria according to the present invention may ingest a low-carbohydrate diet during the course of the treatment. In this specification the term 'low-carbohydrate diet' means a diet generally containing no greater than 50%, such as no greater than 45%, for example no greater than 40%, such as no greater than 35%, for example no greater than 30%, such as no greater than 25%, for example no greater than 20%, such as no greater than 15%, for example no greater than 10%, such as no greater than 5%, for example no greater than 2%, such as no greater than 1%, for example no greater than 0.5%, such as no greater than 0.2% of calories from carbohydrate.

Compositions

While is it possible to administer Bifidobacteria (and, if present, Lactobacilli) alone according to the present invention (i.e. without any support, diluent or excipient), the Bifidobacteria (and, if present, Lactobacilli bacteria) are typically and preferably administered on or in a support as part of a product, in particular as a component of a food product, a dietary supplement or a pharmaceutical formulation. These products typically contain additional components well known to those skilled in the art.

Any product which can benefit from the composition may be used in the present invention. These include but are not limited to foods, particularly fruit conserves and dairy foods and dairy food-derived products, and pharmaceutical products. The Bifidobacteria (and, if present, Lactobacilli) may be referred to herein as "the composition of the present invention" or "the composition".

Food

In one embodiment, the Bifidobacteria (and, if present, Lactobacilli bacteria) are employed according to the invention in a food product such as a food supplement, a drink or a powder based on milk. Here, the term "food" is used in a broad sense—and covers food for humans as well as food for animals (i.e. a feed). In a preferred aspect, the food is for human consumption.

The food may be in the form of a solution or as a solid-depending on the use and/or the mode of application and/or the mode of administration.

When used as, or in the preparation of, a food, such as functional food, the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

Still more preferably the food product employed according to the invention is a fermented milk or humanized milk.

For certain aspects, preferably the present invention may be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

Advantageously, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like. For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a microorganism.

Preferably, the composition is used to ferment milk or sucrose fortified milk or lactic media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$-$10^{10}$ cfu. The microorganism according to the present invention may be used before or after fermentation of the yoghurt.

For some aspects the microorganisms according to the present invention are used as, or in the preparation of, animal feeds, such as livestock feeds, in particular poultry (such as chicken) feed, or pet food.

Advantageously, where the product is a food product, the Bifidobacteria (and, if present, Lactobacilli) should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment.

Food Ingredient

The composition of the present invention may be used as a food ingredient and/or feed ingredient.

As used herein the term "food ingredient" or "feed ingredient" includes a formulation which is or can be added to functional foods or foodstuffs as a nutritional supplement.

The food ingredient may be in the form of a solution or as a solid—depending on the use and/or the mode of application and/or the mode of administration.

Food Supplements

The composition of the present invention may be—or may be added to—food supplements (also referred to herein as dietary supplements).

Functional Foods

The composition of the present invention may be—or may be added to—functional foods.

As used herein, the term "functional food" means food which is capable of providing not only a nutritional effect, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Medicament

The term "medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Pharmaceutical

The composition of the present invention may be used as—or in the preparation of—a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

A pharmaceutically acceptable support may be for example a support in the form of compressed tablets, tablets, capsules, ointments, suppositories or drinkable solutions. Other suitable forms are provided below.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a solution or as a solid—depending on the use and/or the mode of application and/or the mode of administration.

The Bifidobacteria (and, if present, Lactobacilli) of the present invention may be used as pharmaceutical ingredients. Here, the composition may be the sole active component or it may be at least one of a number (i.e. 2 or more) of active components.

The pharmaceutical ingredient may be in the form of a solution or as a solid—depending on the use and/or the mode of application and/or the mode of administration.

The Bifidobacteria (and, if present, Lactobacilli) may be used according to the present invention in any suitable form—whether when alone or when present in a combination with other components or ingredients. The lactic acid bacteria used in the present invention may be referred to herein as "the composition". Likewise, combinations comprising the composition of the present invention and other components and/or ingredients (i.e. ingredients—such as food ingredients, functional food ingredients or pharmaceutical ingredients) may be used in any suitable form.

The Bifidobacteria (and, if present, Lactobacilli) may be used according to the present invention in the form of solid or liquid preparations or alternatives thereof. Examples of solid preparations include, but are not limited to tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even fibre beverages.

Further examples of form include creams. For some aspects the microorganism used in the present invention may be used in pharmaceutical and/or cosmetic creams such as sun creams and/or after-sun creams for example.

In one aspect, the composition according to the present invention may be administered in an aerosol, for example by way of a nasal spray, for instance for administration to the respiratory tract.

Combinations

The composition of the present invention may additionally contain one or more prebiotics. Prebiotics are a category of functional food, defined as non-digestible food ingredients that beneficially affect the host by selectively stimulating the growth and/or activity of one or a limited number of bacteria (particularly, although not exclusively, probiotics, Bifidobacteria and/or lactic acid bacteria) in the colon, and thus improve host health. Typically, prebiotics are carbohydrates (such as oligosaccharides), but the definition does not preclude non-carbohydrates. The most prevalent forms of prebiotics are nutritionally classed as soluble fibre. To some extent, many forms of dietary fibre exhibit some level of prebiotic effect.

In one embodiment, a prebiotic is a selectively fermented ingredient that allows specific changes, both in the composition and/or activity in the gastrointestinal microflora that confers benefits upon host well-being and health.

Suitably, the prebiotic may be used according to the present invention in an amount of 0.01 to 100 g/day, preferably 0.1 to 50 g/day, more preferably 0.5 to 20 g/day. In one embodiment, the prebiotic may be used according to the present invention in an amount of 1 to 10 0 g/day, preferably 2 to 9 g/day, more preferably 3 to 8 g/day. In another embodiment, the prebiotic may be used according to the present invention in an amount of 5 to 50 g/day, preferably 10 to 25 g/day.

Examples of dietary sources of prebiotics include soybeans, inulin sources (such as Jerusalem artichoke, jicama, and chicory root), raw oats, unrefined wheat, unrefined barley and yacon.

Examples of suitable prebiotics include alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, isomaltulose (Palatinose™), isomalto-oligosaccharides, gluco-oligosaccharides, xylo-oligosaccharides, manno-oligosaccharides, beta-glucans, cellobiose, raffinose, gentiobiose, melibiose, xylobiose, cyclodextrins, isomaltose, trehalose, stachyose, panose, pullulan, verbascose, galactomannans, and all forms of resistant starches. A particularly preferred example of a prebiotic is polydextrose.

In some embodiments, a combination of *Bifidobacterium* (and, if present, *Lactobacillus*) bacteria and prebiotics according to the present invention exhibits a synergistic effect in certain applications (i.e. an effect which is greater than the additive effect of the bacteria when used separately). Without wishing to be bound by theory, it is believed that such a combination is capable of selectively stimulating the growth and/or activity of the Bifidobacteria (and, if present, Lactobacilli) bacteria in the colon, and thus improve host health.

In one embodiment, the Bifidobacteria (and, if present, Lactobacilli) may be used according to the present invention in combination with one or more antidiabetic drugs. Examples of oral antidiabetic drugs which may be used in such a combination include biguanides (such as metformin), sulfonylureas (such as carbutamide, chlorpropamide, glibenclamide (Glyburide™), gliclazide, glimepiride, glipizide, gliquidone, tolazamide or tolbutamide), alpha-glucosidase inhibitors (such as acarbose, miglitol or voglibose), thiazolidinediones (TZD) (such as pioglitazone, rivoglitazone or rosiglitazone), meglitinides (such as nateglinide, repaglinide or mitiglinide), dipeptidyl peptidase-4 (DPP-4) inhibitors (such as alogliptin, saxagliptin, sitagliptin or vildagliptin), glucagon-like peptide-1 analogs (such as exenatide, liraglutide, or albiglutide), amylin analogs (such as pramlintide), fast acting insulin analogs (such as insulin lispro, insulin aspart and insulin glulisine), long acting insulin analogs (such as insulin glargine, insulin detemir), dual PPAR agonists (such as aleglitazar) and SGLT2 inhibitors (such as dapagliflozin, remogliflozin and sergliflozin). A particularly preferred example is metformin.

The dosage, mode of administration and formulation of the above antidiabetic drugs for use in the combination of the present invention will be readily apparent to a skilled person. Suitably, the antidiabetic drug may be used according to the present invention in an amount of 1 μg to 10 g/day, preferably 10 μg to 5 g/day, more preferably 0.1 mg to 2 g/day. In one embodiment, the antidiabetic drug may be used according to the present invention in an amount of 1 mg to 1 g/day, preferably 5 to 500 mg/day.

In one embodiment, the Bifidobacteria (and, if present, Lactobacilli) may be used according to the present invention in combination with both a prebiotic (as described and exemplified above) and an antidiabetic drug (as described and exemplified above).

Preferably, the *Bifidobacterium* used in the combination (with a prebiotic, an antidiabetic drug, or both) is of the species *Bifidobacterium animalis*. More preferably, the *Bifidobacterium* used in the combination is of the species *Bifidobacterium animalis* subsp. *lactis*. In a particularly preferred embodiment, the bacteria used in the combination are *Bifidobacterium animalis* subsp. *lactis* strain 420 (B420).

Suitably, the prebiotic used in the combination is polydextrose.

Suitably, the antidiabetic used in the combination is metformin.

In a particularly preferred embodiment, the bacteria used in the combination are *Bifidobacterium animalis* subsp. *lactis* strain 420 (B420), the prebiotic is polydextrose and the antidiabetic is metformin.

In another embodiment, a prebiotic may be used according to the present invention in combination with an antidiabetic drug, but in the absence of Bifidobacteria, Lactobacilli or other bacteria used in the other embodiments of this invention.

Therefore, in a further aspect, the invention comprises a combination of a prebiotic or a mixture thereof and an antidiabetic drug or a mixture thereof.

In a yet further aspect, the invention comprises a food product or food product intermediate including a prebiotic or a mixture thereof and an antidiabetic drug or a mixture thereof.

In a yet further aspect, the invention comprises a pharmaceutical composition comprising a prebiotic or a mixture thereof and an antidiabetic drug or a mixture thereof, together with a pharmaceutically acceptable carrier or diluent.

In one aspect, the invention comprises use of a combination of a prebiotic or a mixture thereof and an antidiabetic drug or a mixture thereof in the manufacture of a food product, dietary supplement or medicament for treating diabetes (preferably but not exclusively Type 2 diabetes) in a mammal.

In another aspect, the invention comprises use of a combination of a prebiotic or a mixture thereof and an antidiabetic drug or a mixture thereof in the manufacture of a food product, dietary supplement or medicament for treating impaired glucose tolerance in a mammal.

In a further aspect, the invention comprises use of a combination of a prebiotic or a mixture thereof and an antidiabetic drug or a mixture thereof in the manufacture of a food product, dietary supplement or medicament for normalising insulin sensitivity in a mammal.

In a yet further aspect, the invention comprises use of a combination of a prebiotic or a mixture thereof and an antidiabetic drug or a mixture thereof in the manufacture of a food product, dietary supplement or medicament for increasing fed insulin secretion in a mammal.

In a still further aspect, the invention comprises use of a combination of a prebiotic or a mixture thereof and an antidiabetic drug or a mixture thereof in the manufacture of a food product, dietary supplement or medicament for decreasing fasted insulin secretion in a mammal.

In an additional aspect, the invention comprises use of a combination of a prebiotic or a mixture thereof and an antidiabetic drug or a mixture thereof in the manufacture of a food product, dietary supplement or medicament for improving glucose tolerance in a mammal.

In a yet further aspect, the invention comprises use of a combination of a prebiotic or a mixture thereof and an antidiabetic drug or a mixture thereof in the manufacture of a food product, dietary supplement or medicament for treating metabolic syndrome in a mammal.

In this embodiment, examples of suitable prebiotics which may be used in such a combination include alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, isomaltulose (Palatinose™), iso-malto-oligosaccharides, gluco-oligosaccharides, xylo-oligo-saccharides, manno-oligosaccharides, beta-glucans, cellobiose, raffinose, gentiobiose, melibiose, xylobiose, cyclodextrins, isomaltose, trehalose, stachyose, panose, pullulan, verbascose, galactomannans, and all forms of resistant starches. A particularly preferred example of a prebiotic is polydextrose.

In this embodiment, examples of oral antidiabetic drugs which may be used in such a combination include biguanides (such as metformin), sulfonylureas (such as carbutamide, chlorpropamide, glibenclamide (Glyburide™), gliclazide, glimepiride, glipizide, gliquidone, tolazamide or tolbutamide), alpha-glucosidase inhibitors (such as acarbose, miglitol or voglibose), thiazolidinediones (TZD) (such as pioglitazone, rivoglitazone or rosiglitazone), meglitinides (such as nateglinide, repaglinide or mitiglinide), dipeptidyl peptidase-4 (DPP-4) inhibitors (such as alogliptin, saxagliptin, sitagliptin or vildagliptin), glucagon-like peptide-1 analogs (such as exenatide, liraglutide, or albiglutide), amylin analogs (such as pramlintide), fast acting insulin analogs (such as insulin lispro, insulin aspart and insulin glulisine), long acting insulin analogs (such as insulin glargine, insulin detemir), dual PPAR agonists (such as aleglitazar) and SGLT2 inhibitors (such as dapagliflozin, remogliflozin and sergliflozin). A particularly preferred example is metformin. The dosage, mode of administration and formulation of the above antidiabetic drugs for use in the combination of this embodiment will be readily apparent to a skilled person.

In this embodiment, the prebiotic used in the combination is preferably polydextrose and the antidiabetic used in the combination is metformin.

In this combination, suitably, the prebiotic may be used in an amount of 0.01 to 100 g/day, preferably 0.1 to 50 g/day, more preferably 0.5 to 20 g/day. In one embodiment, the prebiotic may be used in an amount of 1 to 10 0 g/day, preferably 2 to 9 g/day, more preferably 3 to 8 g/day. In another embodiment, the prebiotic may be used in an amount of 5 to 50 g/day, preferably 10 to 25 g/day.

In this combination, suitably, the antidiabetic drug may be used in an amount of 1 μg to 10 g/day, preferably 10 μg to 5 g/day, more preferably 0.1 mg to 2 g/day. In one embodiment, the antidiabetic drug may be used according to the present invention in an amount of 1 mg to 1 g/day, preferably 5 to 500 mg/day.

Example 1

Materials and Methods

Animal Model and Probiotic Treatment

A cohort of fifty C57Bl/6 10-wk-old male mice were fed a Normal Chow (NC) (A03, SAFE, Augy, France), or a high-fat diet (HFD) (comprising 72% fat (corn oil and lard), 28% protein and <1% carbohydrates) (SAFE, Augy, France) for 4 weeks. This diet has the peculiar advantage to induce diabetes before the onset of obesity (see for example Cani et al. 2008 "Role of gut microflora in the development of obesity and insulin resistance following high-fat diet feeding". Pathol Biol (Paris); Cani et al, *Diabetes* 2008, 57, 1470-81; Knauf et al. *Endocrinology* 2008, 149, 4768-77; Cani et al., *Diabetologia* 2007, 50, 2374-83; Cani et al; *Diabetes* 2007, 56, 1761-1772 and Turini et al. *Swiss Med Wkly* 2007, 137, 700-4).

The mice underwent an intraperitoneal glucose tolerance test. The area under curve was calculated and the mice dispatched homogeneously according to the different experimental groups or ten mice per group (10 mice per group). The mice were fed four more weeks with a normal chow (n=10) or a HFD (n=40). The HFD mice were treated daily for 4 weeks as follows with, 1. Vehicle treated, 2. *Bifidobacterium animalis* subsp. *lactis* strain 420 (B420) ($10^9$/bacteria per mouse), 3. *Lactobacillus acidophilus* NCFM (NCFM) ($10^9$/bacteria per mouse), 4. NCFM+B420 ($5\times10^8$ B420+$5\times10^8$ NCFM per mouse). An intraperitoneal test was then performed as described below. The mice were housed in a controlled environment (inverted 12-h daylight cycle, light off at 10:00 a.m.).

Weight Assessment

Mice were weighed weekly in the beginning of the study diet administration (4 weeks prior to probiotic administration) until 6 weeks into the probiotic treatment (until sacrifice).

Body Composition

Mouse body composition was measured monthly using ECO-MRI. Total body fat mass, total lean body mass, total water mass, free water content, subcutaneous adipose tissue weight, mesenteric adipose tissue weight and liver weight were measured.

Glucose Tolerance

Glucose tolerance was tested after 4-week administration the study diets (before probiotic supplementation) to ensure the glucose-intolerant and diabetic status of the HFD mice, and after 4 weeks of probiotic administration. Briefly, six-hour-fasted mice were injected with 20% glucose (1 g/kg) into the peritoneal cavity. Glycemia was determined with a glucose meter (ACCU-check Active, Roche, Meylan, France) at 30 minutes before the glucose challenge, at the time of the glucose challenge, and 30, 60 and 90 minutes after the glucose challenge, from 3.5 μL of tail-vein tip collected blood.

Plasma Insulin

Insulin concentration was measured from plasma in fasted state as well as in fed state.

Insulin Sensitivity

At completion of the probiotic treatment mice underwent an intrafemoral surgery where a catheter was indwelled for further intravenous infusions. This intravenous intrafemoral catheter was implanted 4 days before the beginning of the experimental day (infusions). The day of the assay the mice were fasted for 5 hours. A hyperinsulinemic euglycemic clamp was performed for 3 hours in the presence of tritiated labeled glucose to determine the glucose turnover rate. Cold glucose was coinfused to maintain euglycemia.

Inflammatory Markers (Real-Time Quantitative PCR)

The inflammation status of adipose, liver and muscle tissue was measured by measuring the concentration of inflammatory markers TNFα, IL-1β, PAI-1, IL6 mRNAs by quantitative RT-PCR analysis. Total mRNAs from the grafted fat pads and the recipient subcutaneous adipose, liver and muscle tissue were extracted using TriPure reagent (Roche, Basel, Switzerland). PCRs were performed using an AbiPrism 7900 Sequence Detection System instrument and software (Applied Biosystems, Foster City, CA, USA, as described in Cani et al. *Diabetes* 2007, 56, 1761-1772. The concentration of each mRNA was normalized for RNA loading for each sample using RPL19 rRNA as an internal standard.

Results

Glucose Tolerance

Figure 2:
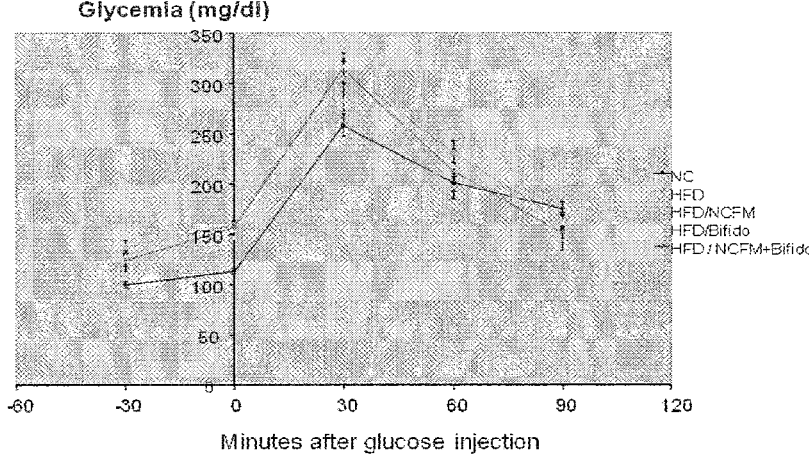
FIG. 2 illustrates the results of an intraperitoneal glucose tolerance test four weeks after the beginning of the probiotic treatment in high fat diet fed mice.

As shown in FIG. 1, all groups of mice fed a high fat diet for 4 weeks were glucose intolerant and diabetic. Following B420 treatment, mice were characterized by an improved glucose tolerance (FIG. 2). Significant decrease is achieved with B420 only; an trend towards health benefit was obtained for NCFM alone or with a combination of NCFM and B420. Therefore it was concluded that the B420 treatment began to improve glucose tolerance. A longer period of treatment could have had a greater impact on the glycemic profiles.

Mouse Body Composition

Figure 3:
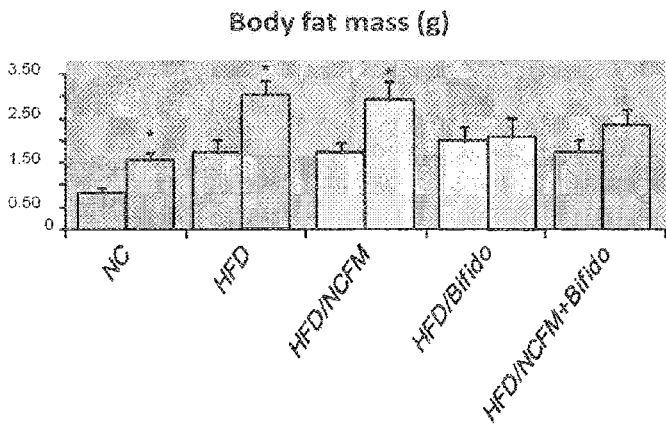
FIG. 3 illustrates the effect of treatment with *Bifidobacterium animalis* subsp. *lactis* strain 420 (B420) *Lactobacillus acidophilus* strain NCFM (NCFM) or a combination of the two (B420+NCFM) on the body fat mass of high fat diet fed mice.
Figure 4:
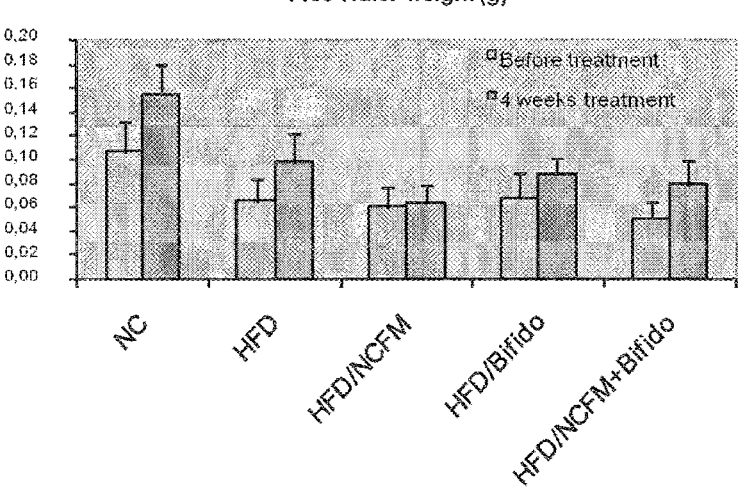
FIG. 4 illustrates the effect of treatment with B420, NCFM or B420+NCFM on the free water weight of high fat diet fed mice.
Figure 5:
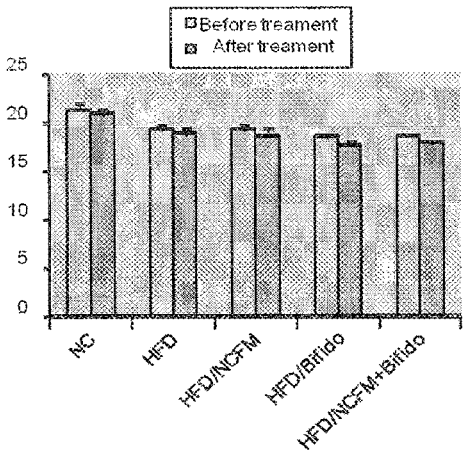
FIG. 5 illustrates the effect of treatment with B420, NCFM or B420+NCFM on the lean body mass weight of high fat diet fed mice.
Figure 6:
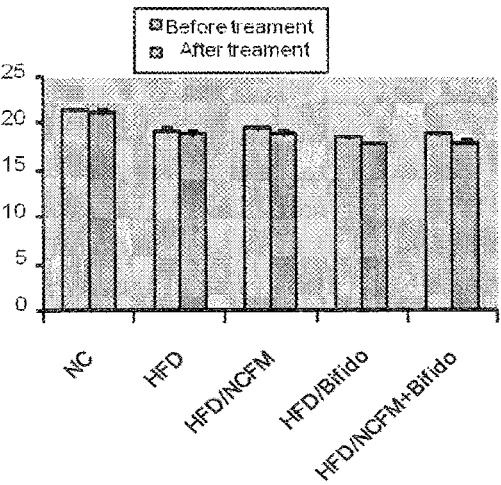
FIG. 6 illustrates the effect of treatment with B420, NCFM or B420+NCFM on the total water weight of high fat diet fed mice.

The data show that four weeks of probiotic treatment with B420 and a combination of B420 and NCFM reduced the impact of HFD on body fat mass increase (FIG. 3). No effect of the treatment on lean body mass, free water mass, and total water mass were observed (FIGS. 4, 5 and 6).

In particular, FIG. 3 illustrates the effect of B420 treatment and combination of B420+NCFM in reducing the impact of high fat diet on the increased body fat mass (wherein the left column signifies the result before treatment and the right column that after treatment). In FIG. 3, * indicates a result significantly different from non treated mice of the same group. A small increase of weight was observed with B420 or with the combination of B420 and NCFM. However, this represents a significant improvement on the untreated HFD mice, as the HFD results show that ingestion of the HFD should increase significantly the body fat mass of the mice.

As the treatment showed no effect on lean body mass, free water mass, and total water mass, it can be concluded from the above that the difference in weight achieved is only related to adipose tissues.

Individual Tissue Weight

Figure 7:
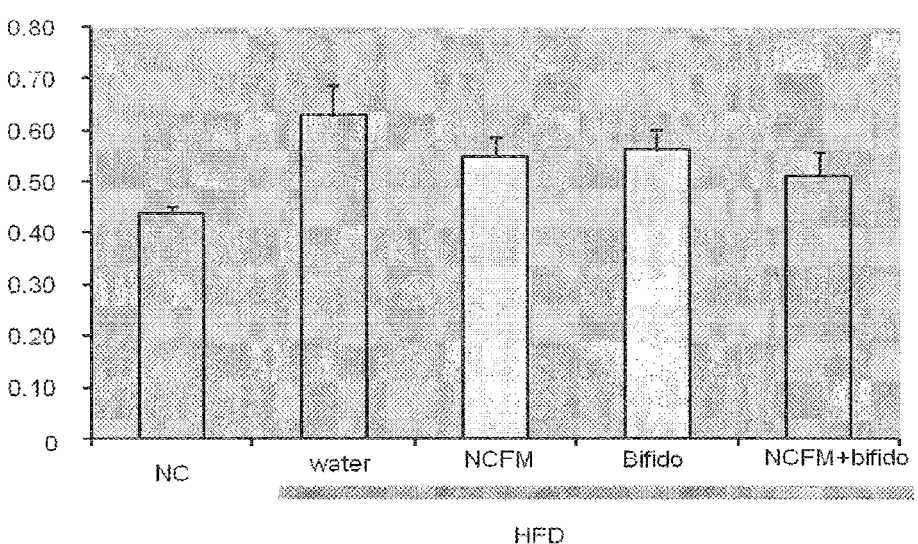
FIG. 7 illustrates the effect of treatment with B420, NCFM or B420+NCFM on the subcutaneous adipose tissue weight of high fat diet fed mice.

The data show that the mesenteric adipose tissue weight was reduced by B420 and B420+NCFM. No differences in subcutaneous adipose tissue or the liver weight were noted (FIGS. 7, 8 and 9).

Figure 8:
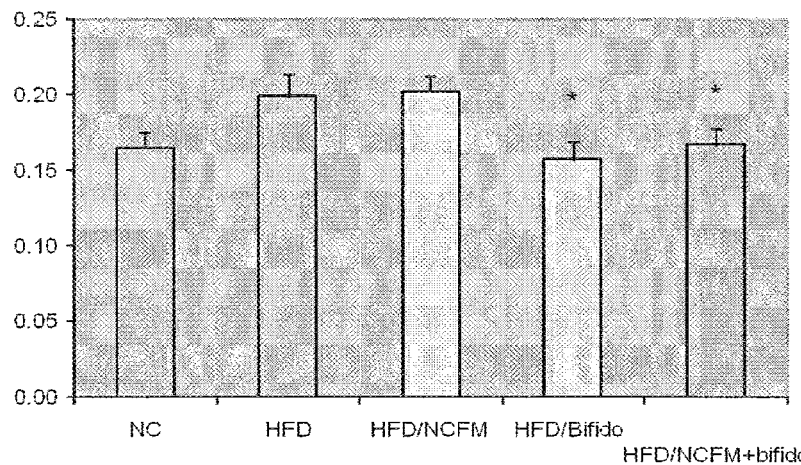
FIG. 8 illustrates the effect of treatment with B420, NCFM or B420+NCFM on the mesenteric adipose tissue weight of high fat diet fed mice.

In particular, FIG. 8 illustrates the effect on mesenteric adipose tissue weight in high-fat diet fed mice treated with probiotics. Significant were achieved for B420 alone or in combination with NCFM (a P value of <0.05 was achieved when compared with the untreated HFD group). The B420 and B420+NCFM treated mice were characterized with less mesenteric fat mass.

Figure 9:
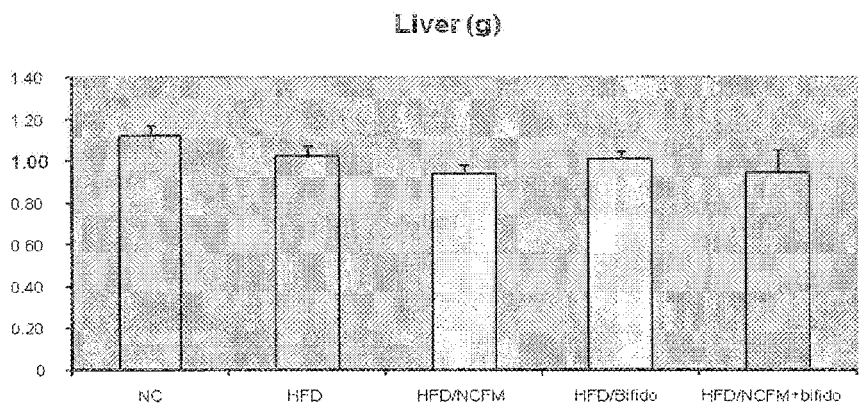
FIG. 9 illustrates the effect of treatment with B420, NCFM or B420+NCFM on the liver weight of high fat diet fed mice.

In addition, FIG. 9 illustrates the effect on liver weight in high fat diet fed mice treated with probiotics. No significant difference was noted, once again showing that the weight difference is not linked with the liver weight.

Weight Gain

Figure 10:
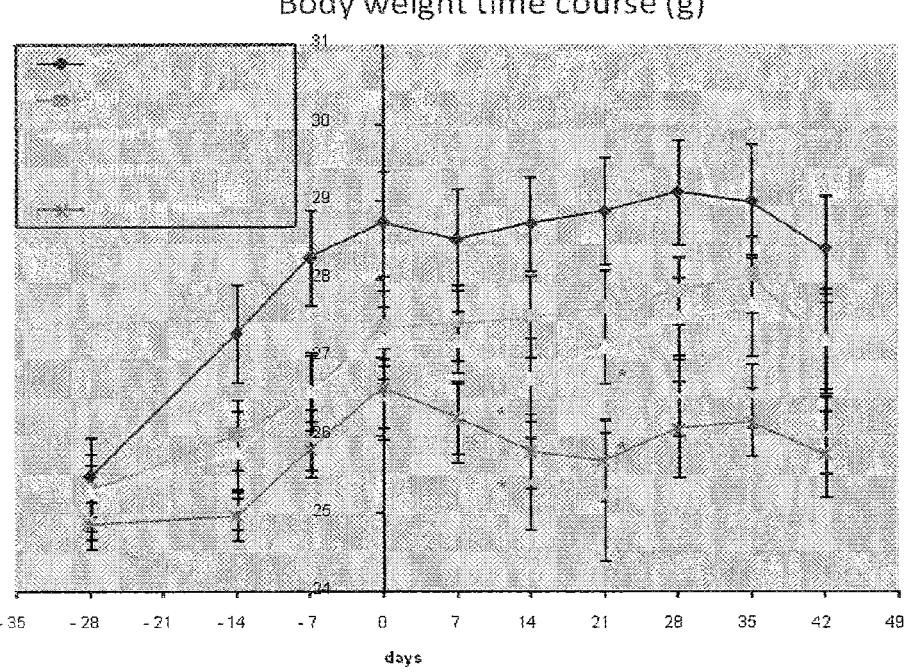
FIG. 10 illustrates the body weight gain before and after treatment with B420, NCFM or B420+NCFM of high fat diet fed mice.

FIG. 10 illustrates the body weight gain before and after probiotic administration of high fat diet fed mice. Body weight gain of the B420 and the B420+NCFM treated mice was lower than that of the mice fed HFD without probiotics or mice treated with NCFM alone. Statistically significant results were achieved for B420 alone or in combination with NCFM; a downward trend (in comparison with untreated HFD-fed mice) was observed for NCFM alone.

Plasma Insulin Concentrations

Figure 11:
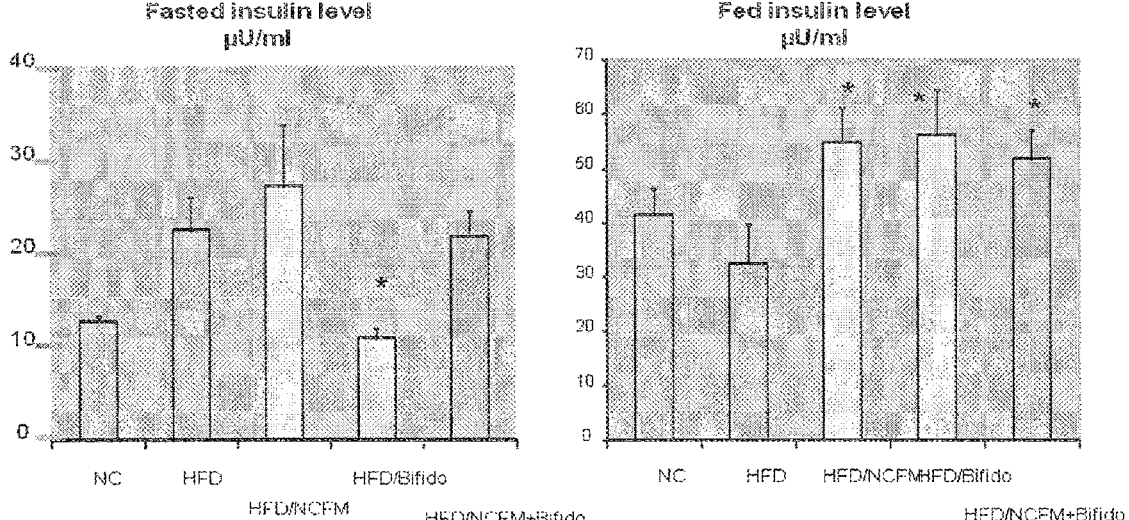
FIG. 11 illustrates the effect of treatment with B420, NCFM or B420+NCFM on the fasted and fed insulin levels of high fat diet fed mice.

Plasma insulin concentration was assessed in the fasted and the fed state. The data show that, in fasting state, the B420 treated group was characterized by a normalization of fasting hyperinsulinemia (FIG. 11). In the fed state all probiotic treatments improved glucose insulin secretion.

These results are of significance, as low levels of insulin (ie base levels of insulin) are observed in the fasted state of healthy, non-diabetic subjects. Statistically significant results were achieved for B420 alone.

Of further significance is that high levels of insulin are observed in the fed state of healthy, non-diabetic subjects. Statistically significant results were achieved for B420 alone, NCFM alone and the combination of the two.

Insulin Sensitivity

Figure 12:
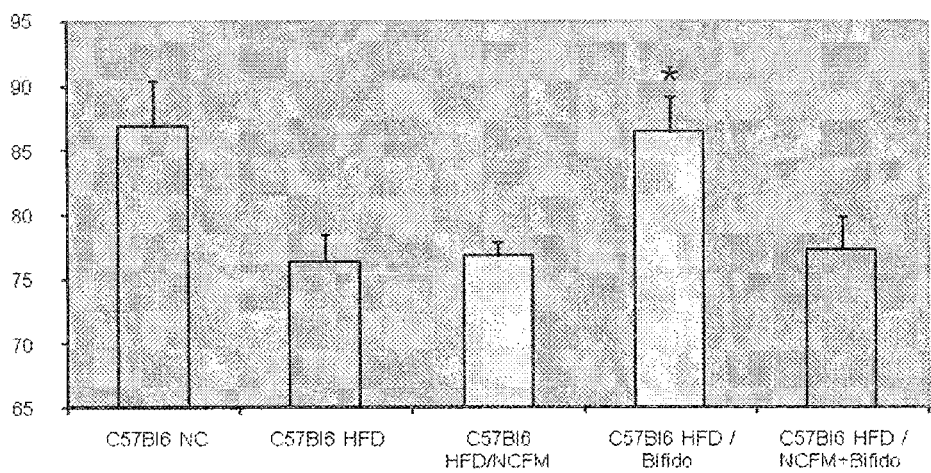
FIG. 12 illustrates the effect of treatment with B420, NCFM or B420+NCFM on the insulin sensitivity of high fat diet fed mice.

FIG. 12 illustrates that high-fat diet fed mice were clamped in hyperinsulinemic euglycemic condition by the clamp method. The data show that B420 treated mice where characterized by a normalization of insulin sensitivity.* $p < 0.05$ vs HFD mice. However, in the presence of NCFM this effect was not observed.

These results are of significance, as insulin sensitivity provides the link between insulin behaviour and consumption of glucose. The results shown with B420 are of particular interest since, in comparison with classic anti-diabetic drugs which target only fasted insulin, insulin sensitivity, or fed insulin, it has an effect on all these factors.

Liver Tissue Inflammation

Figure 13:
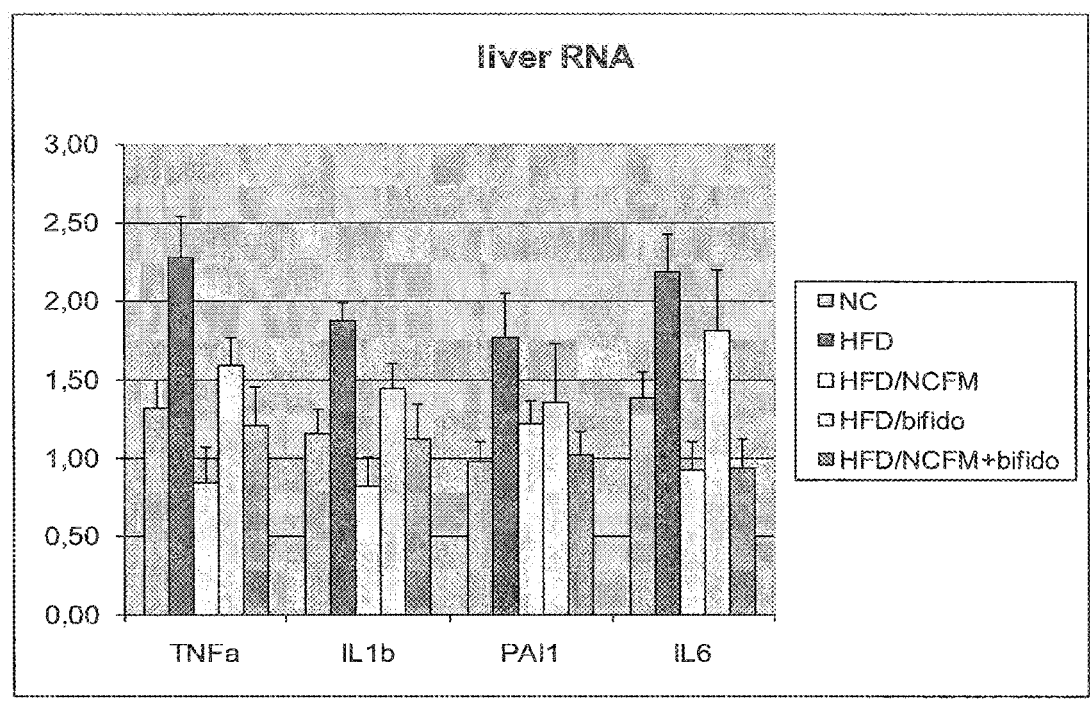
FIG. 13 illustrates the liver cytokine mRNA concentrations in HFD diabetic mice treated with B420, NCFM or B420+NCFM and control HFD-fed mice.
Figure 14:
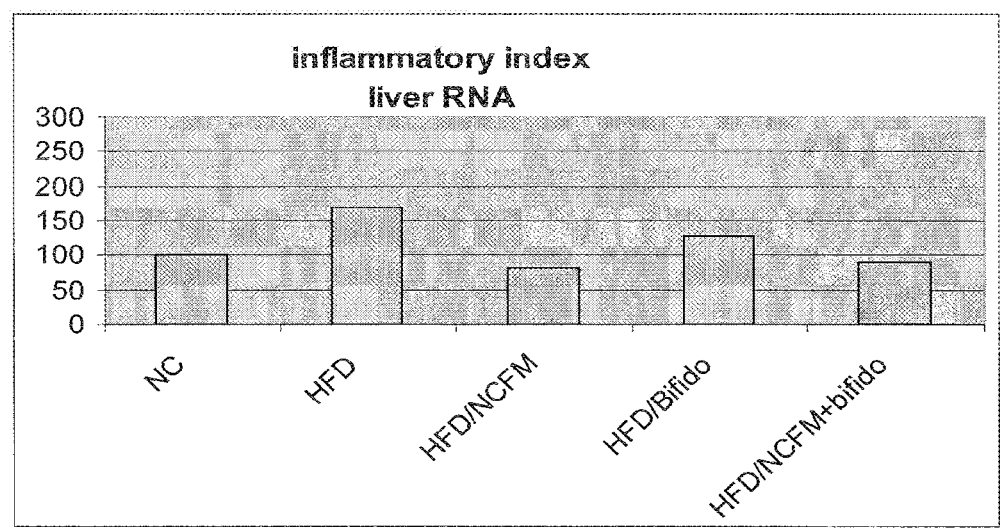
FIG. 14 illustrates the liver tissue inflammatory index in HFD diabetic mice treated with B420, NCFM or B420+NCFM and control HFD-fed mice.

When considering all cytokine mRNA concentrations, HFD induced inflammation in liver tissues (FIGS. 13 and 14). Probiotic treatment had clear anti-inflammatory effect on the liver tissue. This was particularly evident with NCFM treatment. Also treatment with the combination of NCFM and B420 reduced in reduction of inflammation, while B420 treatment alone reduced inflammation to lesser extent.

Muscle Tissue Inflammation

Figure 15:
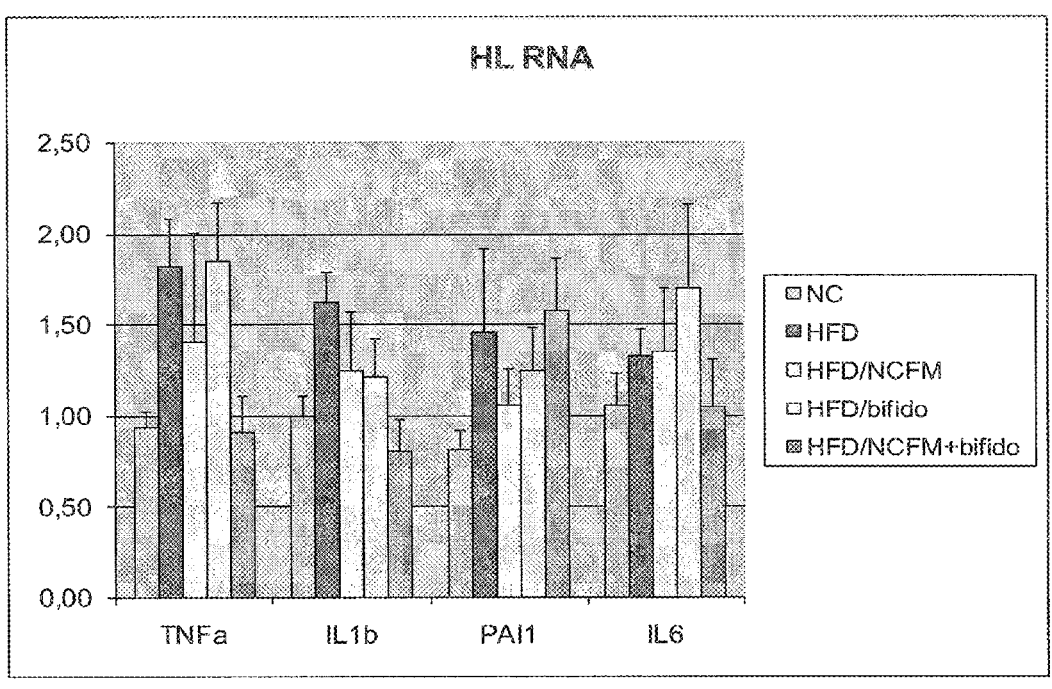
FIG. 15 illustrates the skeletal muscle cytokine mRNA concentrations in HFD diabetic mice treated with B420, NCFM or B420+NCFM and control HFD-fed mice.
Figure 16:
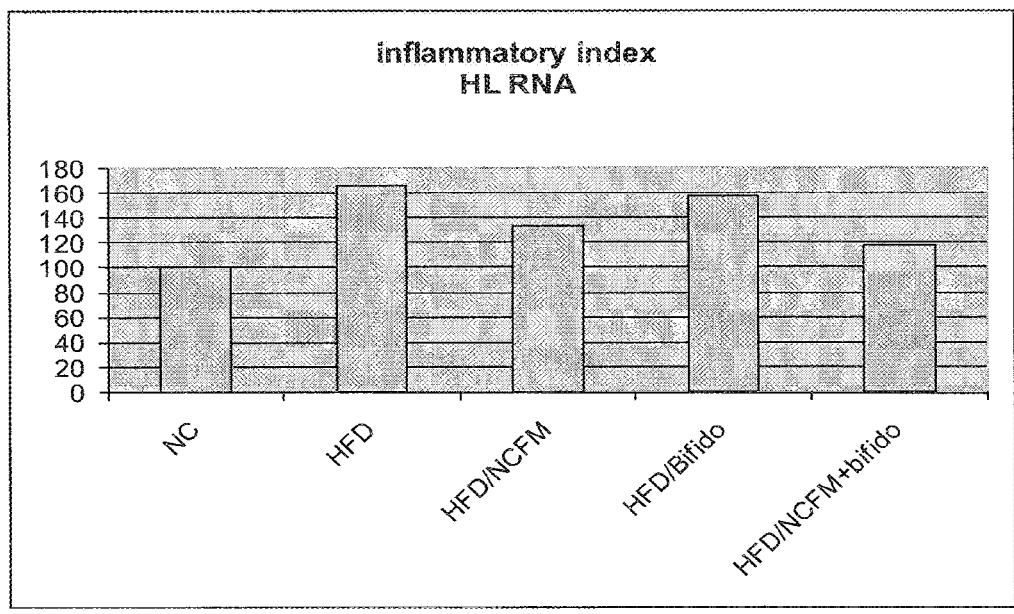
FIG. 16 illustrates the inflammatory index of skeletal muscle tissues in HFD diabetic mice treated with B420, NCFM or B420+NCFM and control HFD-fed mice.

Inflammation was induced by high fat diet also in muscle tissues, although the induction of inflammation was not as strong as in adipose tissue (FIGS. 15 and 16). Probiotic treatment with B420+NCFM and NCFM alone tended to lower muscle tissue inflammation, but the effect was not as clear as with adipose tissue or liver tissue.

Adipose Tissue Inflammation

Figure 17:
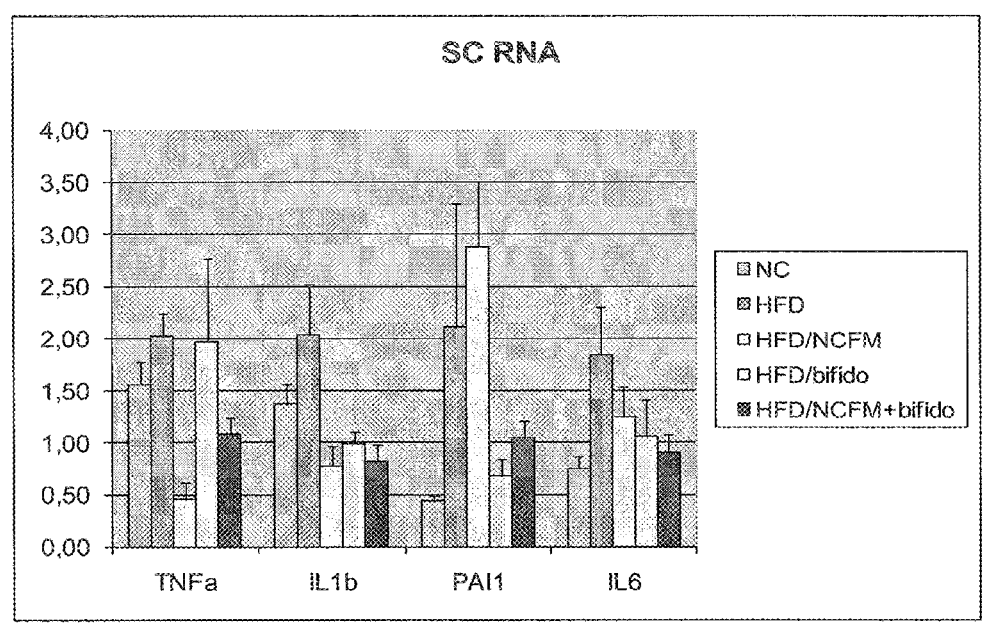
FIG. 17 illustrates the subcutaneous adipose tissue cytokine mRNA concentrations in HFD diabetic mice treated with B420, NCFM or B420+NCFM and control HFD-fed mice.
Figure 18:
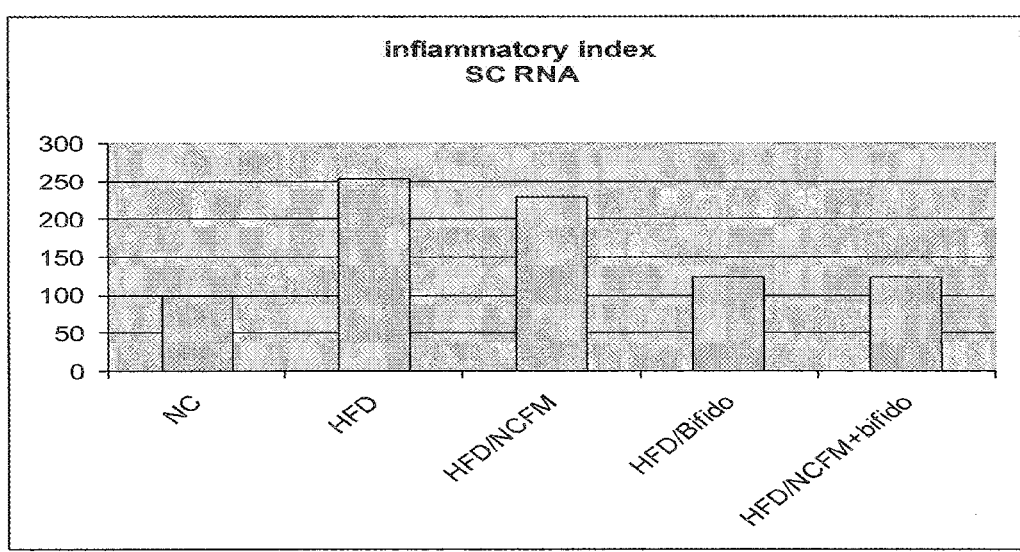
FIG. 18 illustrates the inflammatory index of subcutaneous adipose tissues in HFD diabetic mice treated with B420, NCFM or B420+NCFM and control HFD-fed mice.

The high fat diet clearly induced inflammation in subcutaneous adipose tissue (FIGS. 17 and 18). The B420 treatment and the B420+NCFM treatment both showed strong anti-inflammatory effect. Treatment with NCFM resulted in more inconsistent effects on tissue inflammation but there was a general trend for reduced inflammation.

Taken together, probiotic bacteria showed broad anti-inflammatory effect, with most pronounced effects in adipose tissue and liver tissue. It is notable that the anti-inflammatory effects were differential and dependent on the tissue as well as the probiotic treatment.

Example 2

Materials and Methods

A cohort of C57Bl/6 10-wk-old male mice were a high-fat diet (HFD) (comprising 72% fat (corn oil and lard), 28% protein and <1% carbohydrates) (SAFE, Augy, France) for 4 weeks as described in Example 1. The mice underwent an intraperitoneal glucose tolerance test. The area under curve was calculated and the mice dispatched homogeneously according to the different experimental groups or ten mice per group (10 mice per group). The mice were fed four more weeks with HFD. The HFD mice were treated daily for 4 weeks as follows with B420 ($10^9$ bacteria per mouse), polydextrose (PDX) (0.2 g/day), the antidiabetic drug metformin (MET) (2 mg/mL drinking water), and various combinations of these. Control mice were treated with saline. Mice were housed in a controlled environment (inverted 12-h daylight cycle, light off at 10:00 a.m.). Blood glucose, insulin concentration and HOMA-IR were measured from plasma in fasted state.

Results

Figure 19:
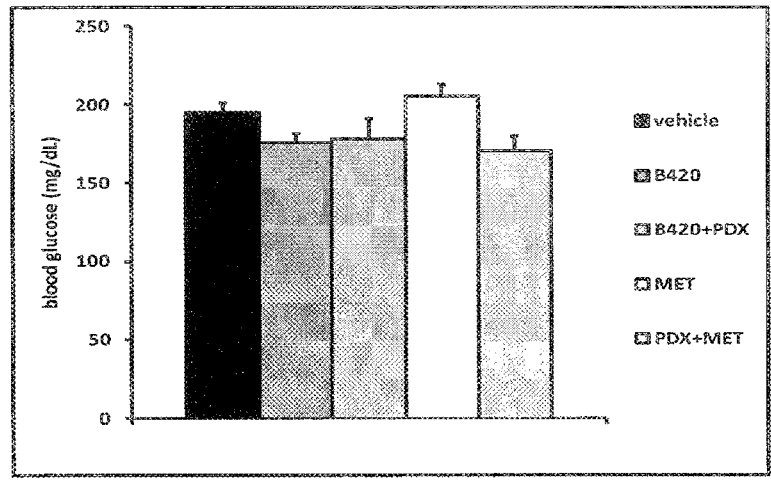
FIG. 19 illustrates the blood glucose levels of HFD-fed mice treated with B420, a combination of B420 with polydextrose (B420+PDX), metformin (MET) or a combination of polydextrose and metformin (PDX+MET) and control HFD-treated mice.

Treatment either with B420 alone or the combination of B420 and polydextrose reduced fasting plasma glucose as compared to control. Metformin alone did not have effect on fasting blood glucose but a combination with metformin and polydextrose was effective (FIG. 19).

Figure 20:
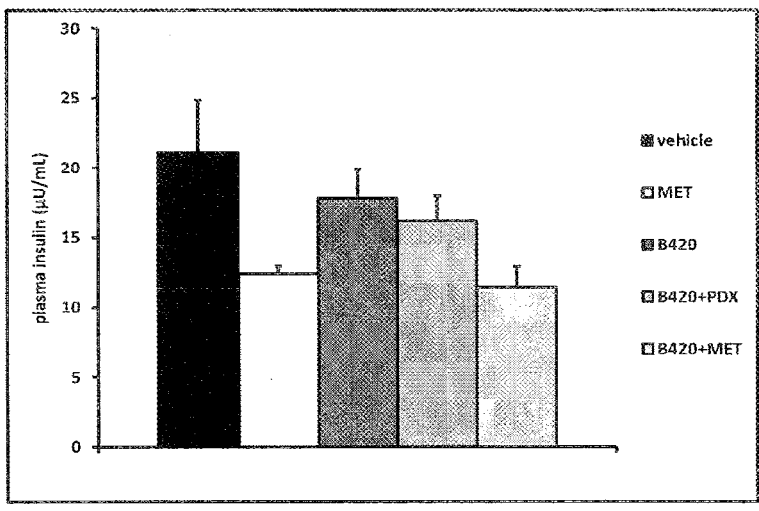
FIG. 20 illustrates the plasma insulin levels of HFD-fed mice treated with B420, B420+PDX, MET or a combination of B420 and metformin (B420+MET) and control HFD-treated mice.

Treatment with B420 reduced fasting plasma insulin. Addition of polydextrose further improved the effect, suggesting a synergistic effect of the combination. Metformin reduced the fasting plasma insulin, but addition of B420 together with metformin further improved the effect (FIG. 20).

Figure 21:
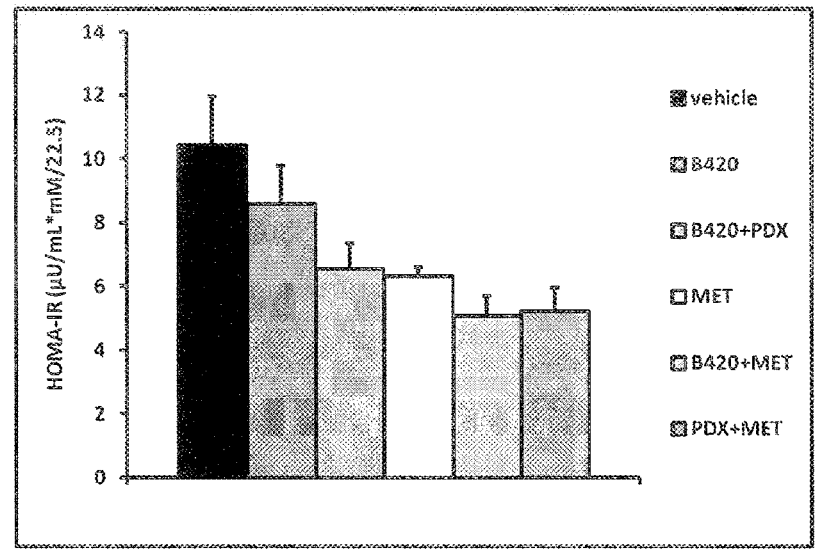
FIG. 21 illustrates the HOMA-IR (homeostatic model of insulin resistance) levels of HFD-fed mice treated with B420, B420+PDX, MET, B420+MET, PDX+MET and control HFD-treated mice.

Treatment with B420 reduced fasting HOMA-IR. Addition of polydextrose with B420 further improved the effect, suggesting a synergistic effect of the combination. Addition of metformin to B420 or B420+polydextrose further improved the effect (FIG. 21).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method of treating a disease or condition in a mammal, wherein the disease or condition is selected from:
   diabetes;
   impaired glucose tolerance;
   reduced insulin sensitivity:
   reduced fed insulin secretion;
   elevated fasted insulin secretion;
   elevated body fat mass; and
   elevated mesenteric fat mass;

and the method comprises:

administering to a mammal in need of such treatment *Bifidobacterium animalis* subsp. *lactis* strain 420 such that an effect of the treatment of the disease or the condition is selected from:

reducing plasma insulin;

reducing body weight gain following a high fat diet;

increasing insulin sensitivity following the high fat diet; or reducing liver and muscle tissue inflammation following the high fat diet.

2. The method of claim 1, wherein: the method comprises treating the diabetes, and the diabetes is Type 2 diabetes.

3. The method of claim 1, wherein the mammal in need of the treatment ingests a high-fat diet.

4. The method of claim 1, further comprising administering metformin in combination with the *Bifidobacterium animalis* subsp. *lactis* strain 420 for reducing fasting plasma insulin.

5. The method of claim 4, further comprising administering polydextrose in combination with the metformin and the *Bifidobacterium animalis* subsp. *lactis* strain 420 for reducing fasting plasma glucose.

6. The method of claim 1, further comprising administering *Lactobacillus acidophilus* strain NCFM (ATCC PTA-4797) in combination with the *Bifidobacterium animalis* subsp. *lactis* strain 420 and the effect is reducing body weight gain following a high fat diet.

7. The method of claim 1, further comprising administering *Lactobacillus acidophilus* strain NCFM (ATCC PTA-4797) in combination with the *Bifidobacterium animalis* subsp. *lactis* strain 420 and the effect is reducing plasma insulin.

8. The method of claim 1, further comprising administering *Lactobacillus acidophilus* strain NCFM (ATCC PTA-4797) in combination with the *Bifidobacterium animalis* subsp. *lactis* strain 420 and the effect is reducing liver and muscle tissue inflammation following the high fat diet.

9. The method of claim 1, wherein the step of administering comprises: providing an effective amount of the *Bifidobacterium animalis* subsp. *lactis* strain 420 at a dosage ranging from $10^6$ Colony-Forming Units to $10^{12}$ Colony-Forming Units of the *Bifidobacterium animalis* subsp. *lactis* strain 420 per dose.

\* \* \* \* \*